United States Patent [19]
Tanaka et al.

[11] Patent Number: 6,127,538
[45] Date of Patent: Oct. 3, 2000

[54] METHOD FOR MODIFYING 1,3,5-TRIAZINE DERIVATIVES

[75] Inventors: Norio Tanaka; Yasuo Fukue; Kenichi Mizusawa; Makoto Ishikawa, all of Funabashi, Japan

[73] Assignee: Nissan Chemical Industries, Ltd., Tokyo, Japan

[21] Appl. No.: 09/091,545

[22] PCT Filed: Dec. 24, 1996

[86] PCT No.: PCT/JP96/03762

§ 371 Date: Jun. 22, 1998

§ 102(e) Date: Jun. 22, 1998

[87] PCT Pub. No.: WO97/24338

PCT Pub. Date: Jul. 10, 1997

[30] Foreign Application Priority Data

Dec. 27, 1995 [JP] Japan ................................. 7-340424

[51] Int. Cl.[7] ...................... C07D 251/42; C07D 251/48; C07D 251/54
[52] U.S. Cl. ............................................ 544/196; 544/197
[58] Field of Search ..................... 544/196, 197

[56] References Cited

U.S. PATENT DOCUMENTS

| | | | |
|---|---|---|---|
| 2,228,161 | 1/1941 | Zerweck et al. | 260/248 |
| 2,385,766 | 9/1945 | Thurston | 117/161 |
| 4,618,676 | 10/1986 | Ebel et al. | 544/196 |
| 4,668,785 | 5/1987 | Ebel et al. | 544/196 |
| 5,534,625 | 7/1996 | Jarman et al. | 544/196 |
| 5,792,867 | 8/1998 | Tanaka et al. | 544/196 |

FOREIGN PATENT DOCUMENTS

| | | |
|---|---|---|
| 3-215564 | 9/1991 | Japan. |
| 8-27125 | 1/1996 | Japan. |
| 8-27128 | 1/1996 | Japan. |
| 8-193071 | 7/1996 | Japan. |
| 8-311029 | 11/1996 | Japan. |
| WO 95/03287 | 2/1995 | WIPO. |
| WO 95/30662 | 11/1995 | WIPO. |

OTHER PUBLICATIONS

Hudlicky, Milos., Reductions in Organic Chemistry, 4–8, 10–12, 40, 49, 62–63, 66–69, 1984.

Paquette L.A., Encyclopedia of Reagents for Organic Synthesis 1257–1258, 3785, 4401–4402, 1995.

Fieser and Fieser, Reagents for Organic Synthesis, vol. 1, p. 140, 1965.

Hofmann, A.W., "Einwirkung des Ammoniaks und der Amine auf den Sulfocyanursauremethylather und das Cyanurchlorid. Normale alkylirte Melamine.," Chem. Ber., vol. 18, pp. 2755–2800 (1885).

Kaiser, Donald W. et al., "Cyanuric Chloride Derivatives. II. Substituted Melamines," J. Amer. Chem. Soc., vol. 73, pp. 2984–2986 (1951).

Lubczak, Jacek, "$^1$H–NMR Study of Reaction of Melamine with Oxiranes," Journal of Applied Polymer Science, vol. 58, 559–564 (1995).

Smolin, Edwin M. et al., "s–Triazines and Derivatives," The Chemistry of Heterocyclic Compounds, Interscience Publishers, Inc., 1959, pp. I–XXIV, 1, 216–269, 308–389.

*Primary Examiner*—Mukund J. Shah
*Assistant Examiner*—V Balasubramanian
*Attorney, Agent, or Firm*—Oliff & Berridge, PLC

[57] ABSTRACT

A method for modifying 1,3,5-triazine derivatives characterized by heating and reacting a 1,3,5-triazine derivatives having at least one amino or mono-substituted amino group on a carbon atom or atoms on its ring with an alcohol in the presence of a metal catalyst and a hydrogen atom to introduce an alkyl group or an alkenyl group into each amino or mono-substituted amino group; another method for modifying 1,3,5-triazine derivatives characterized by heating and reacting a 1,3,5-triazine derivatives having at least one amino or mono-substituted amino group on a carbon atom or atoms on its ring with a dihydric alcohol in the presence of a metal catalyst and a hydrogen atom to introduce an alkyl group having a hydroxyl group into each amino or mono-substituted amino group; and 1,3,5-triazine derivatives obtained by the methods. The various modified sustituted 1,3,5-triazine derivatives thus produced are generally obtained as a mixture. These derivatives can be isolated as compounds having high-purity by a normal separation method for organic compounds, and the compounds are usable in the various applications mentioned in the specification.

15 Claims, No Drawings

METHOD FOR MODIFYING 1,3,5-TRIAZINE DERIVATIVES

This application is a 371 of PCT/JP96/03762, filed Dec. 24, 1996.

TECHNICAL FIELD

In a first aspect, the present invention relates to a method of modifying 1,3,5-triazine derivatives characterized by reacting a 1,3,5-triazine derivative having at least one amino or mono-substituted amino group on a carbon atom or atoms on its ring with an alcohol in the presence of a metal catalyst and hydrogen to introduce an alkyl or alkenyl group into the at least one amino or mono-substituted amino group. And, in a second aspect, the present invention relates to a method of modifying 1,3,5-triazine derivatives as described in claim 1, characterized by reacting a 1,3,5-triazine derivative having at least one amino or mono-substituted amino group on a carbon atom or atoms on its ring with a dihydric alcohol in the presence of a metal catalyst and hydrogen to introduce an alkyl group having a hydroxyl group into the at least one amino or mono-substituted amino group.

The substituted 1,3,5-triazine derivatives obtained by the modification of the amino group or groups attached to the triazine ring carbon or carbons are useful compounds which are used widely as intermediates for various fine chemicals such as agricultural chemicals, medicines, dyes, paints, and the like, as various resin materials, in particular as a component for aminoplast molded materials and also as flame retarding materials.

BACKGROUND ART

As for the synthetic method for substituted triazine derivatives, various synthetic methods have heretofore been known. For example, it has been reported a synthetic method for those compounds of the formula (III)

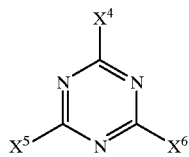

(III)

wherein $X^4$ and $X^5$ represent each a diethylamino group, and $X^6$ represents an ethylamino group, or $X^4$ and $X^5$ represent each an amino group, and $X^6$ represents an ethylamino group or a diethylamino group, which method includes the reaction of 2-chloro-1,3,5-triazine derivative with ethylamine (J. Amer. Chem. Soc., vol. 73, p.2984 (1951)). Those compounds of the formula (III) wherein $X^4$, $X^5$ and $X^6$ represent each an ethylamino group have been reported by a synthetic method which includes reacting 2,4,6-trimethylthio-1,3,5-triazine with ethylamine (Chem. Ber., vol. 18, p.2755 (1885)). Those compounds of the formula (III) wherein $X^4$ represents an amino group, $X^5$ represents an amino group or an octylamino group, and $X^6$ represents an octylamino group have been reported by a synthetic method which includes reacting 2,4,6-triamino-1,3,5-triazine with octylamine hydrochloride (U.S. Pat. No. 2,228,161 (1941)).

Those compounds of the formula (III) wherein $X^4$ represents a phenyl group and $X^5$ and $X^6$ represent each a butylamino group have been reported by a synthetic method which includes reacting 2-phenyl-4,6-diamino-1,3,5-triazine with butylamine (U.S. Pat. No. 2,385,766 (1945)).

Particularly, in recent years, development of compounds introduced with a substituent having a hydroxyl group is becoming increasingly active. For example, there is a description of a compound of the formula (VI)

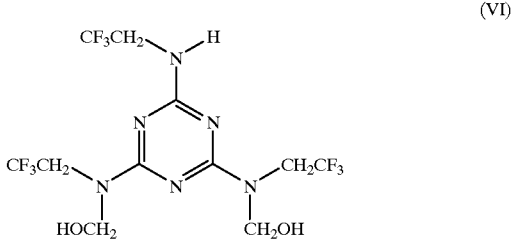

(VI)

having carcinostatic activity (U.S. Pat. No. 5,534,625 (1996)).

Further, it has been reported that compounds of the formula (VII)

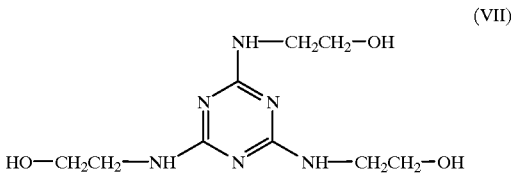

(VII)

are useful as an aminoplast modifier (U.S. Pat. No. 4,668,785. (1987)).

Heretofore, various synthetic methods have been studied for synthesizing these compounds. For example, for the compounds of the formula (VI), there is a report of addition reaction between an N-substituted triazine derivative and formalin (U.S. Pat. No. 5,534,625 (1996).

Furthermore, for the N-substituted triazine derivatives of the formula (VII) having hydroxyethyl groups as a substituent, there is a report of transamination reaction between melamine and ethanolamine (U.S. Pat. No. 4,668,785 (1987)). Similarly, transamination reaction between melamine and isopropanolamine is also reported (U.S. Pat. No. 4,618,676 (1986)).

Also, development has been under way of synthetic methods which catalytically produce various new N-substituted triazine derivatives, such as a method for preparing N-substituted triazine derivatives from a 1,3,5-triazine. derivative, typically melamine, as a starting material and an alcohol proposed by the present inventors (WO 95/03287 (corresponding to JP-A-8-27128)), a method for preparing N-substituted triazine derivatives from an aldehyde and a ketone (WO 95/30662 (corresponding to JP-A-8-193071)), and a method for preparing N-substituted triazine derivatives from an olefin (JP-A-8-27125).

The synthetic method disclosed in J. Amer. Chem. Soc. vol. 73, p.2984 (1954) in most cases needs at least equimolar amount of a condensing agent and generates by-products, such as salts, which would often cause problems in industry. The synthetic method described in Chem. Ber., vol. 18, p.2755 (1885) generates by-products, such as sulfur compounds, which would often cause problems in industry. The synthetic methods disclosed in U.S. Pat. Nos. 2,228,161 and No. 2,385,766, respectively, need high temperatures for reaction and the former by-produces ammonium chloride. It is common in these cases that substitution reaction of releasable groups is performed with substituted amines, which are not inexpensive industrially. This is one of the reasons that prevent N-substituted triazines from being available at low costs.

The method described in U.S. Pat. No. 5,534,625, which is a formalin addition reaction known in the art, is in itself an equilibrium reaction and, hence, the product is obtained in the form of equilibrium composition, so that the yield of the intended compound is not always high.

The methods described in U.S. Pat. Nos. 4,668,785 and No. 4,618,676 are very excellent for introducing hydroxyethyl groups or the like though they involve reactions at high temperatures with acid catalysts. However, when it is attempted to introduce various substituents, the methods are not so suitable since raw materials that are available are restricted and kinds of compounds which can be supplied on an industrial scale at low costs are limited.

It is easy to suppose that in order to incorporate such substituents at a lowest possible cost, it is desirable to use an oxirane derivative or an ethylene glycol derivative (inclusive of oligoethylene glycol) as a raw material. However, there is a report that in the reaction between ethylene oxide and melamine, for example, ring opening addition reaction after the addition reaction with melamine is difficult to control so that the introduction of a polyethylene glycol chain cannot be prevented (J. Appl. Polym. Soc., vol. 58, p.559 (1995)). At present, no satisfactory synthetic method has been known.

Further, the synthetic method for catalytic synthesis of N-substituted triazine derivatives proposed by the present inventors is a manufacturing method which is excellent in that it is conducted industrially at low costs. However, even the method using aldehyde, ketone or the like, which method is considered to be most versatile and excellent among the above-described methods in view of the variety in kind and amount of products and controllability of side reactions, can not to be an ideal one from the viewpoint of process economy because the method involves use of raw materials which has high oxidizability and combustibility and the combination of raw materials having high oxidation degree and reduction conditions. With respect to the introduction of substituents having a hydroxyl group, a modification reaction with an alcohol which can use ethylene glycol derivatives (oligo ethylene glycol or the like) which are available at low costs on an industrial scale is considered suitable. However, in the above-described method which prepares N-substituted triazine derivatives using alcohols (WO95/03287 corresponding to JP-A-8-27128)), the reaction with a dihydric alcohol is not always satisfactory in selectivity, yield, and the like. Accordingly, there is a demand for developing a synthetic method for preparing N-substituted triazine derivatives which has high generality and is excellent from industrial viewpoints.

On the other hand, N-substituted melamine derivatives are compounds which are useful as intermediates for medicines and agricultural chemicals and which are utilized in resin-related fields, such as coatings, adhesives, molding materials, flame retarding materials, and the like based on their excellent characteristics such as reactivity, solubility in solvents, and heat resistance. For example, various 2,4,6-substituted melamine derivatives synthesized from cyanuric chloride can be used as a flame retardant for thermoplastic polymers as described in JP-A-3-215564. Some specific examples described therein are shown below.

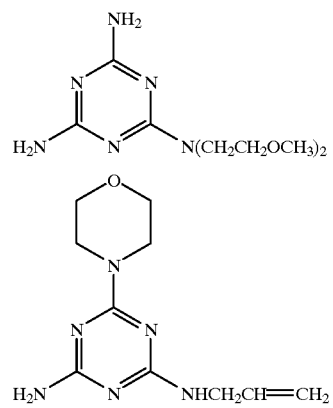

As a result of intensive investigation with view to solving the above-described problems, the present inventors have completed a first invention directed to a method including reacting various alcohols, which are available at low costs on an industrial scale, with an amino group or a mono-substituted amino group on a triazine ring in the presence of a metal catalyst and hydrogen to introduce an alkyl group or an alkenyl group into the amino group or the mono-substituted amino group in high yields, with generating only water as a by-product. Similarly, the present inventors have completed a second invention directed to a method including reacting various ethylene glycol derivatives (oligo ethylene glycol and the like), which are available at low costs on an industrial scale, with an amino group or a mono-substituted amino group on a triazine nucleus in the presence of a metal catalyst and hydrogen to introduce an alkyl group having a terminal hydroxyl group into the amino group or the mono-substituted amino group in high yields, with generating only water as a by-product.

The substituted 1,3,5-triazine derivatives obtained by these reactions considerably inhibit the multimolecular association through intermolecular hydrogen bonding which aminotriazines inherently have and, hence, the derivatives have increased solubilities in various solvents and at the same time decreased melting points, so that their compatibility with other organic compounds also increases. Further, they are compounds which allow ordinary separation/transfer operation such as distillation. In the case of melamine, for example, after the reaction, most part of unreacted melamine precipitates as crystals in the solvent used in the reaction and can be separated by filtration or the like method. On the other hand, the product, most of which is dissolved in the solvent, allows ordinary separation and purification such as solvent extraction or distillation.

An object of the present invention is to provide a method of modifying 1,3,5-triazine derivatives which method can readily prepare substituted 1,3,5-triazine derivatives in high yields, the substituted 1,3,5-triazine derivatives being useful compounds utilized widely as fine chemical intermediates for various agricultural chemicals, medicines, dyes, coatings, and the like or as various resin materials, flame retarding materials, by introducing a substituent into an amino group or a mono-substituted amino group on one or more carbon atoms on the 1,3,5-triazine ring using an alcohol.

DISCLOSURE OF THE INVENTION

Accordingly, in a first aspect, the present invention provides a method of modifying 1,3,5-triazine derivatives, which comprises reacting with an alcohol a 1,3,5-triazine derivative having at least one amino group or mono-substituted amino group attached to a carbon atom on its ring in the presence of a metal catalyst and hydrogen to introduce an alkyl or alkenyl group into the at least one amino group or mono-substituted amino group. Further, in a second aspect, the present invention provides a method of modifying 1,3,5-triazine derivatives, which comprises reacting with a dihydric alcohol a 1,3,5-triazine derivative having at least one amino group or mono-substituted amino group attached to a carbon atom on its ring in the presence of a metal catalyst and hydrogen to introduce an alkyl group having a hydroxyl group into the at least one amino group or mono-substituted amino group.

By the term "modifying an amino group or mono-substituted amino group" as used herein refers to converting the amino group into a mono- or di-substituted amino group, or converting the mono-substituted amino group into a further substituted group, i.e., di-substituted amino group.

Hereafter, the present invention in the first aspect will be described in detail. The 1,3,5-triazine derivatives having at least one amino group or mono-substituted amino group used as a raw material in the present invention according to the first aspect are those 1,3,5-triazine derivatives of the formula (I)

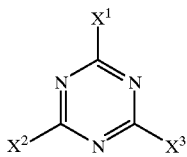
(I)

[wherein at least one of $X^1$, $X^2$ and $X^3$ independently represents an $NHR^1$ group {wherein $R^1$ represents a hydrogen atom, a $C_{1-20}$ alkyl group (where the alkyl group may optionally be substituted with at least one substituent selected from the group consisting of a halogen atom, a $C_{1-6}$ alkoxyl group, a $C_{1-6}$ haloalkoxyl group, a $C_{2-7}$ alkoxycarbonyl group, a $C_{2-7}$ acyloxy group and a phenyl group (where the phenyl group may optionally be substituted with at least one substituent selected from the group consisting of a halogen atom, a $C_{1-6}$ alkyl group, a hydroxyl group and a $C_{1-6}$ alkoxyl group, provided that when plural substituents are present, they may be the same or different), provided that when plural substituents are present, they may be the same or different), a $C_{2-20}$ alkenyl group (where the alkenyl group may optionally be substituted with at least one substituent selected from the group consisting of a halogen atom, a $C_{1-6}$ alkoxyl group, a $C_{1-6}$ haloalkoxyl group, a $C_{2-7}$ alkoxycarbonyl group, a $C_{2-7}$ acyloxy group and a phenyl group (where the phenyl group may optionally be substituted with at least one substituent selected from the group consisting of a halogen atom, a $C_{1-6}$ alkyl group, a hydroxyl group and a $C_{1-6}$ alkoxyl group, provided that when plural substituents are present, they may be the same or different), provided that when plural substituents are present, they may be the same or different), or a phenyl group (where the phenyl group may optionally be substituted with at least one substituent selected from the group consisting of a hydroxyl group, a halogen atom, a $C_{1-6}$ alkoxyl group, a $C_{1-6}$ haloalkoxyl group, a $C_{2-7}$ alkoxycarbonyl group, a $C_{2-7}$ acyloxy group and a phenyl group (where the phenyl group may optionally be substituted with at least one substituent selected from the group consisting of a halogen atom, a $C_{1-6}$ alkyl group, a hydroxyl group and a $C_{1-6}$ alkoxyl group, provided that when plural substituents are present, they may be the same or different), provided that when plural substituents are present, they may be the same or different)};

$X^1$, $X^2$ and $X^3$ other than the at least one of $X^1$, $X^2$ and $X^3$ representing the $NHR^1$ group independently represent an $NR^2R^3$ group {wherein $R^2$ and $R^3$ independently represent a $C_{1-20}$ alkyl group (where the alkyl group may optionally be substituted with at least one substituent selected from the group consisting of a halogen atom, a $C_{1-6}$ alkoxyl group, a $C_{1-6}$ haloalkoxyl group, a $C_{2-7}$ alkoxycarbonyl group, a $C_{2-7}$ acyloxy group and a phenyl group (where the phenyl group may optionally be substituted with at least one substituent selected from the group consisting of a halogen atom, a $C_{1-6}$ alkyl group, a hydroxyl group and a $C_{1-6}$ alkoxyl group, provided that when plural substituents are present, they may be the same or different), provided that when plural substituents are present, they may be the same or different), a $C_{2-20}$ alkenyl group (where the alkenyl group may optionally be substituted with at least one substituent selected from the group consisting of a halogen atom, a $C_{1-6}$ alkoxyl group, a $C_{1-6}$ haloalkoxyl group, a $C_{2-7}$ alkoxycarbonyl group, a $C_{2-7}$ acyloxy group and a phenyl group (where the phenyl group may optionally be substituted with at least one substituent selected from the group consisting of a halogen atom, a $C_{1-6}$ alkyl group, a hydroxyl group and a $C_{1-6}$ alkoxyl group, provided that when plural substituents are present, they may be the same or different), provided that when plural substituents are present, they may be the same or different), or a phenyl group (where the phenyl group may optionally be substituted with at least one substituent selected from the group consisting of a hydroxyl group, a halogen atom, a $C_{1-6}$ alkoxyl group, a $C_{1-6}$ haloalkoxyl group, a $C_{2-7}$ alkoxycarbonyl group, a $C_{2-7}$ acyloxy group and a phenyl group (where the phenyl group may optionally be substituted with at least one substituent selected from the group consisting of a halogen atom, a $C_{1-6}$ alkyl group, a hydroxyl group and a $C_{1-6}$ alkoxyl group, provided that when plural substituents are present, they may be the same or different), provided that when plural substituents are present, they may be the same or different), or $R^2$ and $R^3$ togetehr may form —$(CH_2)_{2-7}$—, —$CH_2CH_2$—NH—$CH_2CH_2$—, —$CH_2CH_2$—N($C_{1-8}$ alkyl)—$CH_2CH_2$—, or —$CH_2CH_2$—O—$CH_2CH_2$—, whose alkylene chain or chains may optionally be substituted with one or two $C_{1-8}$ alkyl groups}, a $C_{1-20}$ alkyl group {wherein the alkyl group may optionally be substituted with at least one substituent selected from the group consisting of a halogen atom, a $C_{1-6}$ alkoxyl group, a carboxyl group, a $C_{2-7}$ alkoxycarbonyl group, a $C_{2-10}$ acyloxy group, and an aryl group (where the aryl group may optionally be substituted with at least one substituent selected from the group consisting of a halogen atom, a $C_{1-6}$ alkyl group, a hydroxyl group, and a $C_{1-6}$ alkoxyl group, provided that when plural substituents are present, they may be the same or different), provided that when plural substituents are present, they may be the same or different}, a $C_{2-20}$ alkenyl group {wherein the alkenyl group may optionally be substituted with at least one substituent selected from the group consisting of a halogen atom, a $C_{1-6}$ alkoxyl group, a carboxyl group, a $C_{2-7}$ alkoxycarbonyl group, a $C_{2-10}$ acyloxy group, and an aryl group (where the aryl group may optionally be substituted with at least one substituent selected from the group consisting of a halogen atom, a $C_{1-6}$ alkyl group, a hydroxyl group, and a $C_{1-6}$ alkoxyl group, provided that when plural substituents are present, they may be the same or different), provided that when plural substituents are present, they may be the same or different}, a phenyl group {wherein the phenyl group may optionally be substituted with at least one substituent selected from the group consisting of a $C_{1-6}$ alkyl group, a halogen atom, a hydroxyl group, a $C_{1-6}$ alkoxyl group, a $C_{2-10}$ acyloxy group, a carboxyl group, a $C_{2-7}$ alkoxycarbonyl group, and an aryl group (where the aryl group may optionally be substituted with at least one substituent selected from the group consisting of a halogen atom, a $C_{1-6}$ alkyl group, a hydroxyl group and a $C_{1-6}$ alkoxyl group, provided that when plural substituents are present, they may be the same or different), provided that when plural substituents are present, they may be the same or different)}, a halogen atom, a $C_{1-10}$ alkoxyl group {wherein the alkoxyl group may be substituted with at least one substituent selected from the group consisting of a halogen atom, a $C_{1-6}$ alkoxyl group, an aryloxy group, a carboxyl group, a $C_{2-7}$ alkoxycarbonyl group, a $C_{2-10}$ acyloxy group, and an aryl group (where the aryl group may optionally be substituted with at least one substituent selected from the group consisting of a halogen atom, a $C_{1-6}$ alkyl group, a hydroxyl group, and a $C_{1-6}$ alkoxyl group, provided that when plural substituents are present, they may be the same or different), provided that when plural substituents are present, they may be the same or different}, or a $C_{1-10}$ alkylthio group {wherein the alkylthio group may be substituted with at least one substituent selected from the group consisting of a halogen atom, a hydroxyl group, a $C_{1-6}$ alkoxyl group, an aryloxy group, a carboxyl group, a $C_{2-7}$ alkoxycarbonyl group, a $C_{2-10}$ acyloxy group, and an aryl group (where the aryl group may optionally be substituted with at least one substituent selected from the group consisting of a halogen atom, a $C_{1-6}$ alkyl group, a hydroxyl group, and a $C_{1-6}$ alkoxyl group, provided that when plural substituents are present, they may be the same or different), provided that when plural substituents are present, they may be the same or different}].

Among the 1,3,5-trizaine derivatives of the formula (I) above, preferably used in the present invention are 1,3,5-triazine derivatives of the 1,3,5-triazine derivatives of the formula (I) in which the $R^1$ group in the $NHR^1$ group represents a hydrogen atom, a $C_{1-20}$ alkyl group {wherein the alkyl group may optionally be substituted with at least one substituent selected from the group consisting of a halogen atom, a $C_{1-6}$ alkoxyl group, and a phenyl group (where the phenyl group may optionally be substituted with at least one substituent selected from the group consisting of a halogen atom, a $C_{1-6}$ alkyl group, a hydroxyl group, and a $C_{1-6}$ alkoxyl group, provided that when plural substituents are present, they may be the same or different), provided that when plural substituents are present, they may be the same or different}, a $C_{2-20}$ alkenyl group {wherein the alkenyl group may optionally be substituted with at least one substituent selected from the group consisting of a halogen atom, a $C_{1-6}$ alkoxyl group, a $C_{1-6}$ haloalkoxyl group, and a phenyl group (where the phenyl group may optionally be substituted with at least one substituent selected from the group consisting of a halogen atom, a $C_{1-6}$ alkyl group, a hydroxyl group, and a $C_{1-6}$ alkoxyl group, provided that when plural substituents are present, they may be the same or different), provided that when plural substituents are present, they may be the same or different}, or a phenyl group (wherein the phenyl group may optionally be substituted with at least one substituent selected from the group consisting of a hydroxyl group, a halogen atom, a $C_{1-6}$ alkoxyl group, and a phenyl group, provided that when plural substituents are present, they may be the same or different), $X^1$, $X^2$ and $X^3$ other than the at least one of $X^1$, $X^2$ and $X^3$ representing the $NHR^1$ group independently represent an $NR^2R^3$ group [wherein $R^2$ and $R^3$ independently represent a $C_{1-20}$ alkyl group {where the alkyl group may optionally be substituted with at least one substituent selected from the group consisting of a halogen atom, a $C_{1-6}$ alkoxyl group, and a phenyl group (where the phenyl group may optionally be substituted with at least one substituent selected from the group consisting of a halogen atom, a $C_{1-6}$ alkyl group, a hydroxyl group, and a $C_{1-6}$ alkoxyl group, provided that when plural substituents are present, they may be the same or different), provided that when plural substituents are present, they may be the same or different}, a $C_{2-20}$ alkenyl group {where the alkenyl group may optionally be substituted with at least one substituent selected from the group consisting of a halogen atom, a $C_{1-6}$ alkoxyl group, and a phenyl group (where the phenyl group may optionally be substituted with at least one substituent selected from the group consisting of a halogen atom, a $C_{1-6}$ alkyl group, a hydroxyl group, and a $C_{1-6}$ alkoxyl group, provided that when plural substituents are present, they may be the same or different), provided that when plural substituents are present, they may be the same or different}, or a phenyl group (where the phenyl group may optionally be substituted with at least one substituent selected from the group consisting of a hydroxyl group, a halogen atom, a $C_{1-6}$ alkoxyl group, and a phenyl group, provided that when plural substituents are present, they may be the same or different), or $R^2$ and $R^3$ together may form $-(CH_2)_{3-6}-$, $-CH_2CH_2-NH-CH_2CH_2-$, $-CH_2CH_2-N(C_{1-8}$ alkyl$)-CH_2CH_2-$, or $-CH_2CH_2-O-CH_2CH_2-$, whose alkylene chain or chains may optionally be substituted with one or two $C_{1-8}$ alkyl groups], a $C_{1-20}$ alkyl group {wherein the alkyl group may optionally be substituted with at least one substituent selected from the group consisting of a halogen atom, a hydroxyl group, a $C_{1-6}$ alkoxyl group, and an aryl group (where the aryl group may optionally be substituted with at least one substituent selected from the group consisting of a halogen atom, a $C_{1-6}$ alkyl group, a hydroxyl group, and a $C_{1-6}$ alkoxyl group, provided that when plural substituents are present, they may be the same or different), provided that when plural substituents are present, they may be the same or different}, a phenyl group (wherein the phenyl group may optionally be substituted with at least one substituent selected from the group consisting of a $C_{1-6}$ alkyl group, a halogen atom, a hydroxyl group, and a $C_{1-6}$ alkoxyl group, provided that when plural substituents are present, they may be the same or different), a halogen atom, or a $C_{1-10}$ alkoxyl group {wherein the alkoxyl group may be substituted with at least one substituent selected from the group consisting of a halogen atom, a hydroxyl group, a $C_{1-6}$ alkoxyl group, and an aryl group (where the aryl group may optionally be substituted with at least one substituent selected from the group consisting of a halogen atom, a $C_{1-6}$ alkyl group, a hydroxyl group, and a $C_{1-6}$ alkoxyl group, provided that when plural substituents are present, they may be the same or different), provided that when plural substituents are present, they may be the same or different}.

Further, preferred 1,3,5-triazine derivatives of the formula (I) above which can be used advantageously in view of easy availability of raw materials, industrially acceptable price and the like include those 1,3,5-triazine derivatives of the formula (I) above in which the $R^1$ group in the $NHR^1$ group represents a hydrogen atom or a $C_{1-20}$ alkyl group (wherein the alkyl group may optionally be substituted with at least one substituent selected from the group consisting of a hydroxyl group, a $C_{1-6}$ alkoxyl group, and a phenyl group, provided that when plural substituents are present, they may be the same or different);

$X^1$, $X^2$ and $X^3$ other than the at least one of $X^1$, $X^2$ and $X^3$ representing the $NHR^1$ group independently represent an $NR^2R^3$ group {wherein $R^2$ and $R^3$ independently represent a $C_{1-20}$ alkyl group (where the alkyl group may optionally be substituted with at least one substituent selected from the group consisting of a hydroxyl group, a $C_{1-6}$ alkoxyl group, and a phenyl group, provided that when plural substituents are present, they may be the same or different) or a phenyl group, or $R^2$ and $R^3$ together may form $-(CH_2)_{4-5}-$, $-CH_2CH_2-NH-CH_2CH_2-$, $-CH_2CH_2-N(C_{1-8}$ alkyl$)-CH_2CH_2-$, or $-CH_2CH_2-O-CH_2CH_2-$, whose alkylene chain or chains may optionally be substituted with one or two $C_{1-8}$ alkyl groups}, a $C_{1-20}$ alkyl group, a phenyl group, or a $C_{1-10}$ alkoxyl group.

As described above, the present reaction may use all the 1,3,5-triazine derivatives having substituents that do not participate in the reaction directly. However, those raw materials which are readily available on an industrial scale include various types of melamine derivatives and of guanamine derivatives, that are available mainly as a major ingredient or modifier for thermosetting resins or a crosslinking agent for baking paints and the method for their synthesis is detailed in, "s-triazines and derivatives, The Chemistry of Heterocyclic Compounds, E. M. Smolin and L. Rapport, Interscience Publishers Inc., New York, 1959."

The alcohol which can be used in the first invention includes alcohols of the formula (II)

$R^4$—OH (II)

[wherein $R^4$ represents a $C_{1-20}$ alkyl group {wherein the alkyl group may optionally be substituted with at least one substituent selected from the group consisting of a halogen atom, a hydroxyl group, a $C_{1-6}$ alkoxyl group, a $C_{1-6}$ haloalkoxyl group, a $C_{2-7}$ alkoxycarbonyl group, a $C_{2-7}$ acyloxy group, and a phenyl group (where the phenyl group may optionally be substituted with at least one substituent selected from the group consisting of a halogen atom, a $C_{1-6}$ alkyl group, a hydroxyl group, and a $C_{1-6}$ alkoxyl group, provided that when plural substituents are present, they may be the same or different), provided that when plural substituents are present, they may be the same or different} or a $C_{2-20}$ alkenyl group {wherein the alkenyl group may optionally be substituted with at least one substituent selected from the group consisting of a halogen atom, a hydroxyl group, a $C_{1-6}$ alkoxyl group, a $C_{1-6}$ haloalkoxyl group, a $C_{2-7}$ alkoxycarbonyl group, a $C_{2-7}$ acyloxy group, and a phenyl group (where the phenyl group may optionally be substituted with at least one substituent selected from the group consisting of a halogen atom, a $C_{1-6}$ alkyl group, a hydroxyl group, and a $C_{1-6}$ alkoxyl group, provided that when plural substituents are present, they may be the same or different), provided that when plural substituents are present, they may be the same or different}].

Among them, those alcohols which can be used advantageously in view of generality, reactivity and the like include alcohols of the formula (II) in which $R^4$ represents a $C_{1-20}$ alkyl group (wherein the alkyl group may optionally be substituted with at least one substituent selected from the group consisting of a halogen atom, a hydroxyl group, a $C_{1-6}$ alkoxyl group, and a phenyl group, provided that when plural substituents are present, they may be the same or different), or a $C_{2-20}$ alkenyl group (wherein the alkenyl group may optionally be substituted with at least one substituent selected from the group consisting of a halogen atom, a hydroxyl group, a $C_{1-6}$ alkoxyl group, and a phenyl group, provided that when plural substituents are present, they may be the same or different).

Further, in view of easy availability of raw materials, industrially acceptable price and the like, alcohols which can be used more advantageously include those alcohols of the formula (II) in which $R^4$ represents a $C_{1-20}$ alkyl group (wherein the alkyl group may optionally be substituted with at least one substituent selected from the group consisting of a halogen atom, a hydroxyl group, a $C_{1-6}$ alkoxyl group, and a phenyl group, provided that when plural substituents are present, they may be the same or different).

Among these, examples of alcohols which are easily available on an industrial scale include methanol, ethanol, n-propanol, isopropanol, n-butanol, sec-butanol, isobutanol, tert-butanol, 1-pentanol, isoamyl alcohol, neopentyl alcohol, n-hexanol, 2-ethylbutanol, methylamyl alcohol, cyclohexanol, n-octanol, 2-ethylhexanol, cyclohexylmethanol, n-nonanol, n-decanol, n-dodecanol, n-hexadecanol, n-octadecanol, ethylene chorohydrin, ethylene bromohydrin, propylene chlorohydrin, propylene bromohydrin, ethylene glycol, propylene glycol, methyl cellosolve, ethyl cellosolve, isopropyl cellosolve, butyl cellosolve, methoxypropylene glycol, ethoxypropylene glycol, butoxypropylene glycol, 3-methoxy-1-butanol, methyl glycolate, ethyl glycolate, tert-butyl glycolate, cyclohexyl glycolate, 2-acetoxyethyl alcohol, 2-propanoyloxyethyl alcohol, 2-benzoyloxyethyl alcohol, 2-methylbenzyl alcohol, 3-methylbenzyl alcohol, 4-methylbenzyl alcohol, 4-ethylbenzyl alcohol, 4-propylbenzyl alcohol, 4-butylbenzyl alcohol, 4-isobutylbenzyl alcohol, 4-chlorobenzyl alcohol, 4-bromobenzyl alcohol, 4-hydroxybenzyl alcohol, 4-methoxybenzyl alcohol, 4-ethoxybenzyl alcohol, 4-butoxybenzyl alcohol, 1-phenethyl alcohol, 2-phenethyl alcohol, allyl alcohol, methallyl alcohol, crotyl alcohol, cinnamyl alcohol, 4-methylcinnamyl alcohol, 4-chlorocinnamyl alcohol, and 2,4-dimethylcinnamyl alcohol.

Although the above-mentioned alcohols may be used in any amounts which may vary depending on the purpose, an effective amount is within the range of generally from 0.01 to 500 moles, practically from 0.1 to 50 moles per mole of 1,3,5-triazine derivative as a raw material from the viewpoints of reactivity and operability. When excess amounts of alcohols are used, it is possible to conduct the process using the alcohols also as a reaction solvent.

The metal catalyst which can be used in the present reaction is preferably those catalysts which contain one or more metals selected from the group consisting of chromium, manganese, iron, cobalt, nickel, copper, niobium, molybdenum, ruthenium, rhodium, palladium, tantalum, iridium, and platinum and more preferably those catalysts which contain one or more metals selected from the group consisting of chromium, manganese, iron, nickel, copper, niobium, molybdenum, ruthenium, rhodium, palladium, tantalum, and iridium.

In particular, in view of the activity for the reaction and industrial economy, are further preferred those catalysts which contain one or more metals selected from the group consisting of chromium, manganese, iron, nickel, copper, molybdenum, ruthenium, palladium, and tantalum.

In this reaction, which is preferable to be conducted in the heterogenous system, it is desirable that the above-described metal catalyst is supplied usually in the form of a solid catalyst. Upon practice, the catalyst may be used either in a fluidized bed or in a fixed bed, both with good results.

The metal catalyst may be in any form of the above-described metals, such as simple element, oxides, hydroxides or salts. Further, one or more metals may be used. When two or more metals are used, they can be used as a multi-element catalyst in various forms, such as alloys, intermetallic compounds, mixtures of various metal compounds. In addition to the above-described metal species, other trace metal components may also be added for highly increasing and stabilizing the catalyst activity and preventing deterioration and deactivation of the catalyst.

It is practically desirable to use the metal catalysts as a carried catalyst. In this case, generally used in industry and desirable carriers are non-amorphous or amorphous oxides of silicon, aluminum and the like, such as silica, alumina, aluminosilicate, silica-alumina, zeolite, diatomaceous earth, and clay mineral, inorganic salts such as calcium carbonate, barium carbonate, barium sulfate, and active carbon.

More specifically, examples of the catalyst include chromium oxide, manganese oxide, manganese oxide on silica, Raney iron, ferrous oxide, ferric oxide, ferric oxide on silica, Raney cobalt, cobalt oxide, Raney nickel, nickel oxide, nickel on silica, nickel on alumina, nickel on active carbon, nickel chloride, copper oxide, niobium oxide, molybdenum oxide, molybdenum oxide on silica, ruthenium on silica, ruthenium on alumina, ruthenium on active carbon, ruthenium oxide, ruthenium black, palladium on silica, palladium on alumina, palladium on active carbon, palladium on barium sulfate, palladium on zeolite, palladium on silica-alumina, palladium chloride, palladium oxide, tantalum oxide, rhodium on silica, rhodium on alumina, rhodium on active carbon, rhodium on chloride, rhodium oxide, iridium on silica, iridium on alumina, iridium on active carbon, iridium chloride, iridium oxide, platinum on silica, platinum on alumina, platinum on active carbon, platinum chloride, platinum oxide (Adam's catalyst), platinum black, copper-chromium based catalysts, and copper-nickel based catalysts.

The catalysts described above may be used either singly or in combination as a multi-element catalyst.

The amount of the metal catalyst to be used may be in the range of normally from 0.00001 to 20 mol %, preferably from 0.0001 to 10 mol %, based on the triazine derivative of the formula (I) above.

It may be sometimes preferable to add one or more additives to the above-described catalyst before the reaction is carried out according to the necessity. Examples of such an additive include mono- and multi-dentate tertiary phosphines, such as trimethylphosphine, triethylphosphine, tributylphosphine, triphenylphosphine, tris(p-tolyl)phosphine, tris(2,6-dimethylphenyl)phosphine, sodium diphenylphosphino-benzene-3-sulfonate, bis(3-sulfonate-phenyl)phosphinobenzene sodium salt, 1,2-bis(diphenylphosphino)ethane, 1,3-bis(diphenylphosphino)propane, 1,4-bis(diphenyl-phosphino)butane, and tris(3-sulfonate-phenyl)phosphine sodium slat, phosphorous acid esters such as triethyl phosphite, tributyl phosphite, triphenyl phosphite, and tris(2,6-dimethylphenyl)phosphite, phosphonium salts such as triphenylmethylphosphonium iodide, triphenylmethylphosphonium bromide, triphenylmethylphosphonium chloride, triphenylallylphosphonium iodide, triphenylallylphosphonium bromide, triphenylallylphosphonium chloride, tetraphenylphosphonium iodide, tetraphenylphosphonium bromide, and tetraphenylphosphonium chloride, phosphoric acid esters such as triphenyl phosphate, trimethyl phosphate, triethyl phosphate, and triallyl phosphate, unsaturated hydrocarbons such as cyclooctadiene and cyclopentadiene, nitrites such as benzonitrile and acetonitrile, ketones such as acetylacetone and dibenzylidene acetone.

The amount of additive to be added may be within the range of usually from 0.01 to 10000 mol %, preferably 1 to 5000 mol %, per mol of metal catalyst.

The reaction can proceed at reaction temperatures of usually from 100° C. to 500° C., and preferred reaction temperature is 150 to 400° C. in view of reaction rate, productivity, utility, and the like.

It is desirable to set up reaction conditions so that the reaction time, which may depend on the reactivity of the triazine derivatives of the formula (I) above, can be set to usually 0.1 to 100 hours, preferably 1 to 20 hours.

The present reaction can proceed in the absence of solvents. However, solvents may be used, if desired, for improving operability or the like.

No particular limitation is posed on the solvent as far as they are inert to the reaction; for example, ethers such as tetrahydrofuran, diethyl ether, dimethoxymethane, dimethoxyethane, diethoxymethane, diethoxyethane, ethylene glycol dimethyl ether, ethylene glycol diethyl ether, ethylene glycol dibutyl ether, diethylene glycol diethyl ether, and 1,4-dioxane, aromatic hydrocarbons such as benzene, toluene, xylene, mesitylene, cumene, chlorobenzene, o-dichlorobenzene, m-dichlorobenzene, p-dichlorobenzene, and tetrahydronaphthalene, aliphatic hydrocarbons such as pentane, hexane, cyclohexane, heptane, octane, and decane, nitriles such as acetonitrile and propionitrile, esters such as methyl acetate, ethyl acetate, butyl acetate, ethyl propionate, methyl benzoate, and ethyl benzoate, amides such as N,N-dimethylformamide, N,N-dimethylacetamide, and N-methylpyrrolidone, ureas such as 1,3-dimethyl-imidazolidinone, and N,N,N',N'-tetramethylurea, and water. These may be used singly or in combination. An excess amount of alcohols of the formula (II) above may be used as a solvent.

The feature of the present reaction is to carry out it in a reducing atmosphere in the presence of hydrogen in the reaction system. The present inventors have found that copresence of hydrogen in the reaction system obviates the tendencies that in the absence of hydrogen, by-products are generated in large amounts upon dehydrogenation reaction of the alcohol used as a raw material and that the yield of the intended products is decreased considerably. Accordingly, the hydrogen-copresent reaction of the present invention allows the alkylation reaction to proceed preferentially for modifying only the nitrogen atom or atoms of the amino group or mono-substituted amino group on the carbon atom or atoms of 1,3,5-triazine ring, so that the conversion and recovery of the triazine derivative used can be increased to a large extent.

For the means for making hydrogen to exist in the reaction system, various methods may be used. It is generally desirable to treat a metal catalyst is treated in a hydrogen atmosphere in advance or treat the reaction itself in hydrogen gas or in a hydrogen-containing gas atmosphere, as simple methods. When hydrogen gas or hydrogen-containing gases are used, the hydrogen partial pressure thereof that is preferred practically is from 0.01 to 500 kg/cm², and more preferably from 0.1 to 200 kg/cm² for industrial applications. In the case of hydrogen-containing gases, various gases can be used as a diluent gas as far as they do not participate in the reaction directly. While inert gases such as nitrogen, argon, and helium are generally used, carbon monoxide, carbon dioxide, ammonia gas, air, and the like can also be used for the purpose of stabilization of the products and catalysts as well.

When the mixed gases as described above are used, there is no problem if the hydrogen partial pressure is sufficient for the reaction. It is desirable that the reaction proceed at a total pressure of from 0.1 to 500 kg/cm², preferably from 0.5 to 300 kg/cm².

When the present reaction is conducted at high temperatures, the alcohol, solvent, and the like used will generate autogenous pressures and thus, it is desirable for practical operation to set the total pressure of the reaction system to 300 kg/cm² or less inclusive of such autogenous pressures.

As treatments after completion of the reaction, the reaction product can be under high degree of purification, and purified and isolated with ease by removing unreacted triazines by crystallization, filtration or the like means followed by distilling off the solvent, as needed, or extracting the product with a two phase system of water-organic solvent, and recrystallization, distillation, separation by chromatography, salt formation, and so on. The metal catalyst can be separated by filtration or the like, recovered and reused, if necessary.

The present reaction gives rise to a series of compounds with sequentially increasing degree of modification depending on the number of amino groups or substituted amino groups which can react, their reactivity, or progress of the reaction, and, hence, generally several kinds of products are obtained as a mixture and the composition of the mixture can be controlled to some extent by controlling the reaction conditions. Although for some applications of the substituted 1,3,5-triazine derivatives, the product obtained by the production method of the first invention may be used as a mixture as it is, it is also possible to separate or isolate the intended products as substances having high purity or as absolutely pure substances by the above-described generally used post-treatments, if necessary, before using it.

The substituted 1,3,5-triazine derivatives, obtained by the modification method of modifying the amino group or groups on the carbon atom or atoms on the 1,3,5-triazine ring according to the first invention as described above, are 1,3,5-triazine derivatives of the formula (III)

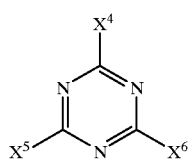

(III)

[wherein at least one of $X^4$, $X^5$ and $X^6$ independently represents an $NR^5R^6$ group {wherein $R^5$ and $R^6$ independently represents a hydrogen atom, a $C_{1-20}$ alkyl group (where the alkyl group may optionally be substituted with at least one substituent selected from the group consisting of a halogen atom, a hydroxyl group, a $C_{1-6}$ alkoxyl group, a $C_{1-6}$ haloalkoxyl group, a $C_{2-7}$ alkoxycarbonyl group, a $C_{2-7}$ acyloxy group and a phenyl group (where the phenyl group may optionally be substituted with at least one substituent selected from the group consisting of a halogen atom, a $C_{1-6}$ alkyl group, a hydroxyl group, and a $C_{1-6}$ alkoxyl group, provided that when plural substituents are present, they may be the same or different), provided that when plural substituents are present, they may be the same or different), a $C_{2-20}$ alkenyl group (where the alkenyl group may optionally be substituted with at least one substituent selected from the group consisting of a halogen atom, a hydroxyl group, a $C_{1-6}$ alkoxyl group, a $C_{1-6}$ haloalkoxyl group, a $C_{2-7}$ alkoxycarbonyl group, a $C_{2-7}$ acyloxy group, and a phenyl group (where the phenyl group may optionally be substituted with at least one substituent selected from the group consisting of a halogen atom, a $C_{1-6}$ alkyl group, a hydroxyl group, and a $C_{1-6}$ alkoxyl group, provided that when plural substituents are present, they may be the same or different), provided that when plural substituents are present, they may be the same or different), or $R^5$ and $R^6$ together may form —$(CH_2)_{2-7}$—, —$CH_2CH_2$—NH—$CH_2CH_2$—, —$CH_2CH_2$—$N(C_{1-8}$ alkyl)—$CH_2CH_2$—, or —$CH_2CH_2$—O—$CH_2CH_2$—, whose alkylene chain or chains may optionally be substituted with one or two $C_{1-8}$ alkyl groups}, a $C_{1-20}$ alkyl group {where the alkyl group may optionally be substituted with at least one substituent selected from the group consisting of a halogen atom, a $C_{1-6}$ alkoxyl group, a carboxyl group, a $C_{2-7}$ alkoxycarbonyl group, a $C_{2-10}$ acyloxy group, and an aryl group (where the aryl group may optionally be substituted with at least one substituent selected from the group consisting of a halogen atom, a $C_{1-6}$ alkyl group, a hydroxyl group, and a $C_{1-6}$ alkoxyl group, provided that when plural substituents are present, they may be the same or different), provided that when plural substituents are present, they may be the same or different), a $C_{2-20}$ alkenyl group {where the alkenyl group may optionally be substituted with at least one substituent selected from the group consisting of a halogen atom, a $C_{1-6}$ alkoxyl group, a carboxyl group, a $C_{2-7}$ alkoxycarbonyl group, a $C_{2-10}$ acyloxy group, and an aryl group (where the aryl group may optionally be substituted with at least one substituent selected from the group consisting of a halogen atom, a $C_{1-6}$ alkyl group, a hydroxyl group, and a $C_{1-6}$ alkoxyl group, provided that when plural substituents are present, they may be the same or different), provided that when plural substituents are present, they may be the same or different}, a phenyl group {where the phenyl group may optionally be substituted with at least one substituent selected from the group consisting of a $C_{1-6}$ alkyl group, a halogen atom, a hydroxyl group, a $C_{1-6}$ alkoxyl group, an aryloxy group, a $C_{2-10}$ acyloxy group, a carboxyl group, a $C_{2-7}$ alkoxycarbonyl group, and an aryl group (where the aryl group may optionally be substituted with at least one substituent selected from the group consisting of a halogen atom, a $C_{1-6}$ alkyl group, a hydroxyl group, and a $C_{1-6}$ alkoxyl group, provided that when plural substituents are present, they may be the same or different), provided that when plural substituents are present, they may be the same or different}, a halogen atom, a $C_{1-10}$ alkoxyl group {wherein the alkoxyl group may be substituted with at least one substituent selected from the group consisting of a halogen atom, a $C_{1-6}$ alkoxyl group, an aryloxy group, a carboxyl group, a $C_{2-7}$ alkoxycarbonyl group, a $C_{2-10}$ acyloxy group, a $C_{2-12}$ dialkylamino group, and an aryl group (where the aryl group may optionally be substituted with at least one substituent selected from the group consisting of a halogen atom, a $C_{1-6}$ alkyl group, a hydroxyl group, and a $C_{1-6}$ alkoxyl group, provided that when plural substituents are present, they may be the same or different), provided that when plural substituents are present, they may be the same or different}, or a $C_{1-10}$ alkylthio group {wherein the alkylthio group may be substituted with at least one substituent selected from the group consisting of a halogen atom, a hydroxyl group, a $C_{1-6}$ alkoxyl group, an aryloxy group, a carboxyl group, a $C_{2-7}$ alkoxycarbonyl group, a $C_{2-10}$ acyloxy group, and an aryl group (where the aryl group may optionally be substituted with at least one substituent selected from the group consisting of a halogen atom, a $C_{1-6}$ alkyl group, a hydroxyl group, and a $C_{1-6}$ alkoxyl group, provided that when plural substituents are present, they may be the same or different), provided that when plural substituents are present, they may be the same or different}].

Among the 1,3,5-trizaine derivatives included by the formula (I) above, preferred in view of their generality are those substituted 1,3,5-triazine derivatives of the formula (I) in which the $R^5$ and $R^6$ in the $NR^5R^6$ group represented by $X^4$, $X^5$, and $X^6$ represent independently a hydrogen atom, a $C_{1-20}$ alkyl group {wherein the alkyl group may optionally be substituted with at least one substituent selected from the group consisting of a halogen atom, a hydroxyl group, a $C_{1-6}$ alkoxyl group, and a phenyl group (where the phenyl group may optionally be substituted with at least one substituent selected from the group consisting of a halogen atom, a $C_{1-6}$ alkyl group, a hydroxyl group, and a $C_{1-6}$ alkoxyl group, provided that when plural substituents are present, they may be the same or different), provided that when plural substituents are present, they may be the same or different}, or a $C_{2-20}$ alkenyl group {wherein the alkenyl group may optionally be substituted with at least one substituent selected from the group consisting of a halogen atom, a hydroxyl group, a $C_{1-6}$ alkoxyl group, and a phenyl group (where the phenyl group may optionally be substituted with at least one substituent selected from the group consisting of a halogen atom, a $C_{1-6}$ alkyl group, a hydroxyl group, and a $C_{1-6}$ alkoxyl group, provided that when plural substituents are present, they may be the same or different), provided that when plural substituents are present, they may be the same or different}, or $R^5$ and $R^6$ together may form —(CH$_2$)$_{3-6}$—, —CH$_2$CH$_2$—NH—CH$_2$CH$_2$—, —CH$_2$CH$_2$—N(C$_{1-8}$ alkyl)—CH$_2$CH$_2$—, or —CH$_2$CH$_2$—O—CH$_2$CH$_2$—, whose alkylene chain or chains may optionally be substituted with one or two $C_{1-8}$ alkyl groups}, $X^4$, $X^5$, and $X^6$ other than the $NR^5R^6$ group independently represent a $C_{1-20}$ alkyl group {where the alkyl group may optionally be substituted with at least one substituent selected from the group consisting of a halogen atom, a hydroxyl group, a $C_{1-6}$ alkoxyl group, and an aryl group (where the aryl group may optionally be substituted with at least one substituent selected from the group consisting of a halogen atom, a $C_{1-6}$ alkyl group, a hydroxyl group, and a $C_{1-6}$ alkoxyl group, provided that when plural substituents are present, they may be the same or different), provided that when plural substituents are present, they may be the same or different}, a phenyl group (where the phenyl group may optionally be substituted with at least one substituent selected from the group consisting of a $C_{1-6}$ alkyl group, a halogen atom, a hydroxyl group, and a $C_{1-6}$ alkoxyl group, provided that when plural substituents are present, they may be the same or different), a halogen atom, or a $C_{1-10}$ alkoxyl group {where the alkoxyl group may optionally be substituted with at least one substituent selected from the group consisting of a halogen atom, a hydroxyl group, a $C_{1-6}$ alkoxyl group, and an aryl group (where the aryl group may optionally be substituted with at least one substituent selected from the group consisting of a halogen atom, a $C_{1-6}$ alkyl group, a hydroxyl group, and a $C_{1-6}$ alkoxyl group, provided that when plural substituents are present, they may be the same or different), provided that when plural substituents are present, they may be the same or different}.

Further, 1,3,5-triazine derivatives which are preferred in view of industrial and practical effects are those substituted 1,3,5-triazine derivatives of the formula (III) wherein the $R^5$ and $R^6$ in the $NR^5R^6$ group represented by $X^4$, $X^5$, and $X^6$ represent independently a hydrogen atom, a $C_{1-20}$ alkyl group (wherein the alkyl group may optionally be substituted with at least one substituent selected from the group consisting of a hydroxyl group, a $C_{1-6}$ alkoxyl group, and a phenyl group, provided that when plural substituents are present, they may be the same or different), or $R^5$ and $R^6$ together may form —(CH$_2$)$_{4-5}$—, —CH$_2$CH$_2$—NH—CH$_2$CH$_2$—, —CH$_2$CH$_2$—N(C$_{1-8}$ alkyl)—CH$_2$CH$_2$—, or —CH$_2$CH$_2$—O—CH$_2$CH$_2$—, whose alkylene chain or chains may optionally be substituted with one or two $C_{1-8}$ alkyl groups, $X^4$, $X^5$, and $X^6$ other than the $NR^5R^6$ group independently represent a $C_{1-20}$ alkyl group, a phenyl group, or a $C_{1-10}$ alkoxyl group.

As described above, in the first invention, it is possible to use various compounds as raw material 1,3,5-triazine derivatives and alcohols. The products obtained by the method of the first invention include various 1,3,5-triazine derivatives with various substituents depending on the combination of 1,3,5-triazine derivatives and alcohols as raw materials.

As described in the foregoing, typical examples of raw material 1,3,5-triazine derivative include melamine, various melamine derivatives, various guanamine derivatives and examples of the alcohol include alcohols derived from various petroleum chemical products and typical products can be obtained by combining these. Further, the substituted melamine derivatives prepared by modifying melamine according to the method of the first invention can be used as raw material 1,3,5-triazine derivatives for use in the first invention as far as they have an —NH— group on at least one of the carbon atoms on the ring.

While it is not intended to limit the raw materials which can be used in the present reaction to those of a specific range based on their price and ease in availability, specific examples of raw materials and substituents in products will be described below in order to further elucidate the scope of the reaction of the present invention.

In the formulae, the substituents represented by $X^1$, $X^2$, and $X^3$ in the formula (I) for raw materials and the substituents represented by $X^4$, $X^5$ and $X^6$ in the formula (III) for products, examples of NHR$^1$, NR$^2$R$^3$, and NR$^5$R$^6$ include an amino group, a methylamino group, an ethylamino group, an isopropylamino group, an n-butylamino group, an i-butylamino group, a sec-butylamino group, a tert-butylamino group, a cyclohexylamino group, a cyclohexylmethylamino group, an n-octylamino group, an n-decylamino group, an n-hexadecylamino group, an n-octadecylamino group, a 2-ethyl-1-hexylamino group, an N,N-dimethylamino group, an N,N-diethylamino group, an N,N-diisopropylamino group, an N,N-di-n-butylamino group, an N,N-di-i-butylamino group, an N,N-di-sec-butylamino group, an N-methyl-N-tert-butylamino group, an N-methyl-N-cyclohexylamino group, a 4-methylcyclohexylamino group, an N,N- dicyclohexylamino group, an N,N-di-n-octylamino group, an N,N-dicyclo-hexylmethylamino group, an N,N-bis(2-ethyl-1-hexyl)amino group, a chloroethylamino group, a 3-chloropropylamino group, a hydroxyethylamino group, a 1-hydroxy-2-propylamino group, a 2-hydroxy-1-propylamino group, a 4-hydroxybutylamino group, a 5-hydroxypentylamino group, an N,N-bis(hydroxyethyl)amino group, a trifluoroethylamino group, a 2-trifluoropropylamino group, a 2-ethoxyethylamino group, a 3-methoxypropylamino group, a 2-pentyloxyethylamino group, a 3-cyclohexyloxy-propylamino group, a 2-chloroethoxyethylamino group, a 5-monofluoropentyloxypentylamino group, a 2-methoxycarbonylethylamino group, a 2-ethoxycarbonylethylamino group, a tert-butoxycarbonylethylamino group, a 2-cyclohexyloxycarbonylethylamino group, an acetoxymethylamino group, a 3-acetoxypropylmethylamino group, a cyclo-hexanoyloxyethylamino group, a 2-benzoyloxypropylamino group, an o-tolylamino group, an m-tolylamino group, a p-tolylamino group, a benzylamino group, a dibenzylamino group, an N-benzyl-N'-methylamino group, a 2-phenylethylamino group, a 3-(4-chlorophenyl)propylamino group, a 2-(4-cyclohexylphenyl)ethylamino group, a 2-(3-fluorophenyl)-pentylamino group, a 4-methoxybenzylamino group, a 2-chloro-4-fluorobenzylamino group, a 3,5-dimethylbenzylamino group, a 4-cyclopentyloxybenzylamino group, a 2-(2-chloro-4-fluoro-5-isopropylphenyl)propylamino group, a 4-hydroxylbenzylamino group, a 4-hydroxyphenylethylamino group, an allylamino group, a methallylamino group, a crotylamino group, a 3-cyclopentenylamino group, a 3-cyclohexenylamino group, a 3-(6-trifluoromethyl)-cyclohexenylamino group, a diallylamino group, a dimethallylamino group, a 3-(1-methoxy)allyl group, a chloromethoxyethylamino group, an ethoxycarbonylallylamino group, a cinnamylamino group, a 4-chlorocinnamylamino group, an N-(4-methylcinnamyl)-N-methylamino group, and a 4-methoxycinnamylamino group.

Further, specific examples of the substituent in a case that $R^2$ and $R^3$ in the $NR^2R^3$ are bound or in a case that $R^5$ and $R^6$ in the $NR^5R^6$ group are bound include an aziridino group, an azetidino group, a pyrrolidino group, a pyrrolyl group, a piperidino group, a dihydropyrrolyl group, a dihydropyridyl group and a morpholino group.

Among other substituents represented by $X^1$, $X^2$, $X^3$, $X^4$, $X^5$, and $X^6$, the $C_{1-20}$ alkyl group which may be substituted includes a methyl group, an ethyl group, an n-propyl group, an n-butyl group, an i-butyl group, a sec-butyl group, an n-amyl group, an i-amyl group, a hexyl group, a cyclohexyl group, a cyclohexylmethyl group, a heptyl group, an octyl group, a 2-ethylhexyl group, a nonyl group, a decyl group, a hexadecyl group, an octadecyl group, a trifluoromethyl group, a 3-chloropropyl group, a 2-trifluoromethylethyl group, a hydroxymethyl group, a 2-hydroxyethyl group, a methoxymethyl group, a methoxyethyl group, an ethoxymethyl group, a cyclohexylmethoxyethyl group, a 2-carboxyethyl group, a 3-carboxypropyl group, a methoxycarbonylmethyl group, a methoxycarbonylethyl group, a tert-butyoxycarbonylmethyl group, a cyclohexyloxycarbonylethyl group, an acetyloxymethyl group, a benzoyloxymethyl group, a 3-(tert-butylcarbonyloxy)propyl group, a benzyl group, a 4-methylbenzyl group, a 4-methoxybenzyl group, a 2-chloro-4-fluorobenzyl group, a 3,5-dimethylbenzyl group, a 4-cyclopentyloxybenzyl group, and the like.

The $C_{2-20}$ alkenyl group which may be substituted include a vinyl group, an isopropenyl group, a 1-butenyl group, a 3-hexenyl group, an allyl group, a methallyl group, a crotyl group, a 2-chloroallyl group, a methoxyvinyl group, an ethoxyvinyl group, a cyclohexylvinyl group, a 4-phenyl-2-butenyl group, a 2-carboxyvinyl group, an ethoxycarbonylvinyl group, a tert-butoxycarbonylvinyl group, an acetyloxyvinyl group, a cyclohexanoyloxyvinyl group, a cinnamyl group, a 4-chlorocinnamyl group, a 3,5-dimethoxycinnamyl group, a 2,4,6-trimethylcinnamyl group, a styryl group, a 2,4-dichlorostyryl group, a 6-dodecene-1-yl group, a 1,2-diphenylvinyl group, and the like.

The phenyl group which may be substituted includes a phenyl group, a p-tolyl group, a m-tolyl group, an o-tolyl group, a 3,5-dimethylphenyl group, a 4-cyclohexylphenyl group, a 2,4,6-trimethylphenyl group, a 2-methyl-4-isoropylphenyl group, a 2-chlorophenyl group, a 2,4-dichlorophenyl group, a 2-fluoro-4-chlorophenyl group, a 3,5-dimethoxyphenyl group, a 4-cyclopentyloxyphenyl group, a m-phenoxyphenyl group, a 4-(2-naphthyloxy)phenyl group, a 3-acetoxyphenyl group, a 3-benzoyloxyphenyl group, a 4-carboxyphenyl group, a 4-methoxycarbonylphenyl group, a 3-cyclohexyloxycarbonylphenyl group, a 4-acetyloxyphenyl group, a 3-cyclohexylcarbonyloxyphenyl group, a 4-biphenyl group, a 4-(2-naphthyl)phenyl group, a 4-(4-chlorophenyl)phenyl group, a 4-(5-(1-methyl-3-chloropyrazol)-yl)phenyl group, and the like.

The halogen atom includes a fluorine atom, a chlorine atom, a bromine atom, and an iodine atom.

The $C_{1-10}$ alkoxyl group which may be substituted includes a methoxy group, an ethoxy group, an n-propyloxy group, an i-propyloxy group, an n-butyloxy group, an i-butyloxy group, a sec-butyloxy group, a tert-butyloxy group, an n-amyloxy group, an i-amyloxy group, a hexyloxy group, a cyclohexyloxy group, a cyclohexylmethyloxy group, a heptyloxy group, an octyloxy group, a 2-ethylhexyloxy group, a nonyloxy group, a decyloxy group, a hexadecyloxy group, an octadecyloxy group, a trifluoromethyloxy group, a 3-chloropropyloxy group, a 2-trifluoromethylethyloxy group, a methoxymethoxy group, a methoxyethoxy group, an ethoxymethoxy group, a cyclohexylmethoxyethoxy group, a 2-carboxyethoxy group, a 3-carboxypropoxy group, a methoxycarbonylmethoxy group, a methoxycarbonylethoxy group, a tert-butoxycarbonylmethoxy group, a cyclohexyloxycarbonylethoxy group, an acetyloxymethyloxy group, a benzoyloxymethyloxy group, a 3-(tert-butylcarbonyloxy)propyloxy group, a benzyloxy group, a 4-methylbenzyloxy group, a 4-methoxybenzyloxy group, a 2-chloro-4-fluorobenzyloxy group, a 3,5-dimethylbenzyloxy group, and a 4-cyclopentyloxybenzyloxy group, and the like.

The $C_{1-10}$ alkylthio group which may be substituted includes a methylthio group, an ethylthio group, an n-propylthio group, an i-propylthio group, an n-butylthio group, an i-butyltio group, a sec-butylthio group, a tert-butylthio group, an n-amylthio group, an i-amylthio group, a hexylthio group, a cyclohexylthio group, a cyclohexylmethylthio group, a heptylthio group, an octylthio group, a 2-ethylhexylthio group, a nonylthio group, a decylthio group, a hexadecylthio group, an octadecylthio group, a trifluoromethylthio group, a 3-chloropropylthio group, a 2-trifluoromethylethylthio group, a methoxy-methylthio group, a methoxyethylthio group, an ethoxy-methylthio group, a cyclohexylmethoxyethylthio group, a 2-carboxyethylthio group, a 3-carboxypropylthio group, a methoxycarbonylmethylthio group, a methoxycarbonylethylthio group, a tert-butoxycarbonylmethylthio group, a cyclo-hexyloxycarbonylethylthio group, an acetyloxymethylthio group, a benzoyloxymethylthio group, a 3-(tert-butylcarbonyloxy)propylthio group, a benzylthio group, a 4-methylbenzylthio group, a 4-methoxybenzylthio group, a 2-chloro-4-fluorobenzylthio group, a 3,5-dimethylbenzylthio group, a 4-cyclopentyloxybenzylthio group, and the like.

These examples of substituents are typical ones and the present invention is by no means limited thereto.

Next, the present invention in the second aspect will be described in detail. The 1,3,5-triazine derivatives having at least one amino group or mono-substituted amino group, raw material for use in the present invention in the second aspect, are those 1,3,5-triazine derivatives of the formula (I)

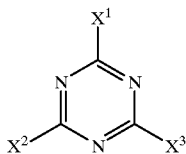

(I)

[wherein at least one of $X^1$, $X^2$ and $X^3$ independently represents an $NHR^1$ group {wherein $R^1$ represents a hydrogen atom, a $C_{1-20}$ alkyl group (where the alkyl group may optionally be substituted with at least one substituent selected from the group consisting of a halogen atom, a $C_{1-6}$ alkoxyl group, a $C_{2-6}$ dialkylamino group, a $C_{2-7}$ alkoxycarbonyl group, and a phenyl group, provided that when plural substituents are present, they may be the same or different) or a phenyl group (where the phenyl group may optionally be substituted with at least one substituent selected from the group consisting of a halogen atom, a $C_{1-6}$ alkyl group, a $C_{1-6}$ alkoxyl group, and a $C_{1-6}$ haloalkoxyl group, provided that when plural substituents are present, they may be the same or different)}, $X^1$, $X^2$ and $X^3$ other than the at least one of $X^1$, $X^2$ and $X^3$ representing the $NHR^1$ group independently represent an $NR^2R^3$ group {wherein $R^2$ and $R^3$ independently represent a $C_{1-20}$ alkyl group (where the alkyl group may optionally be substituted with at least one substituent selected from the group consisting of a halogen atom, a $C_{1-6}$ alkoxyl group, a $C_{2-6}$ dialkylamino group, a $C_{2-7}$ alkoxycarbonyl group, and a phenyl group, provided that when plural substituents are present, they may be the same or different), or a phenyl group (where the phenyl group may optionally be substituted with at least one substituent selected from the group consisting of a halogen atom, a $C_{1-6}$ alkyl group, a $C_{1-6}$ alkoxyl group, and a $C_{1-6}$ haloalkoxyl group, provided that when plural substituents are present, they may be the same or different), or $R^2$ and $R^3$ together may form a 3- to 6-membered cyclic structure containing atoms freely selected from a carbon atom, an oxygen atom, and a nitrogen atom}].

Further, 1,3,5-triazine derivatives of the formula (I) above which can be used more advantageously include those 1,3,5-triazine derivatives of the formula (I) above in which the $R^1$ group in the $NHR^1$ group represents a hydrogen atom, a $C_{1-20}$ alkyl group (where the alkyl group may optionally be substituted with at least one substituent selected from the group consisting of a halogen atom, a $C_{1-6}$ alkoxyl group and a phenyl group, provided that when plural substituents are present, they may be the same or different), or a phenyl group (where the phenyl group may optionally be substituted with at least one substituent selected from the group consisting of a halogen atom, a $C_{1-6}$ alkyl group and a $C_{1-6}$ haloalkoxyl group, provided that when plural substituents are present, they may be the same or different), $X^1$, $X^2$ and $X^3$ other than the at least one of $X^1$, $X^2$ and $X^3$ representing the $NHR^1$ group described above independently represent an $NR^2R^3$ group (wherein $R^2$ and $R^3$ independently represent a $C_{1-20}$ alkyl group (where the alkyl group may optionally be substituted with at least one substituent selected from the group consisting of a halogen atom, a $C_{1-6}$ alkoxyl group and a phenyl group, provided that when plural substituents are present, they may be the same or different), or a phenyl group (where the phenyl group may optionally be substituted with at least one substituent selected from the group consisting of a halogen atom, a $C_{1-6}$ alkyl group and a $C_{1-6}$ haloalkoxyl group, provided that when plural substituents are present, they may be the same or different), or $R^2$ and $R^3$ together may form a 3- to 6-membered cyclic structure containing atoms freely selected from a carbon atom, an oxygen atom, and a nitrogen atom)}.

Further, 1,3,5-triazine derivatives of the formula (I) above which can be used further more advantageously include those 1,3,5-triazine derivatives of the formula (I) above in which the $R^1$ group in the $NHR^1$ group represents a hydrogen atom, a $C_{1-20}$ alkyl group, or a phenyl group, $X^1$, $X^2$ and $X^3$ other than the at least one of $X^1$, $X^2$ and $X^3$ representing the $NHR^1$ group described above independently represent an $NR^2R^3$ group (wherein $R^2$ and $R^3$ independently represent a $C_{1-20}$ alkyl group, or a phenyl group, or $R^2$ and $R^3$ together may form a 3- to 6-membered cyclic structure containing atoms freely selected from a carbon atom and a nitrogen atom)}.

Furthermore, the 1,3,5-triazine derivative of the formula (I) above which can be used most advantageously in view of ease in availability of and of industrially acceptable price of raw materials is melamine.

As described above, the present reaction may use all the 1,3,5-triazine derivatives having substituents that do not participate in the reaction directly. However, those raw materials which are readily available on an industrial scale include various types of melamine derivatives and of guanamine derivatives, that are available mainly as a major ingredient or modifier for thermosetting resins or a crosslinking agent for baking paints and the method for their synthesis is detailed in, "s-triazines and derivatives, The Chemistry of Heterocyclic Compounds, E. M. Smolin and L. Rapport, Interscience Publishers Inc., New York, 1959". The alcohol which can be used in the second invention includes dihydric alcohols of the formula (IV)

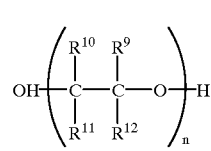

(IV)

[wherein $R^9$, $R^{10}$, $R^{11}$, and $R^{12}$, independently represent a hydrogen atom or a $C_{1-10}$ alkyl group (wherein the alkyl group may optionally be substituted with at least one substituent selected from the group consisting of a halogen atom and a phenyl group, provided that when plural substituents are present, they may be the same or different), and n is an integer of from 1 to 10].

Among them, those dihydric alcohols which can be used advantageously in view of generality, reactivity and the like include alcohols represented by the formula (IV) in which $R^9$, $R^{10}$, $R^{11}$, and $R^{12}$ independently represent a hydrogen atom or a $C_{1-5}$ alkyl group (wherein the alkyl group may optionally be substituted with at least one substituent selected from the group consisting of a halogen atom and a phenyl group, provided that when plural substituents are present, they may be the same or different) and n is an integer of from 1 to 5.

Dihydric alcohols which can be used more advantageously include those dihydric alcohols of the formula (IV) in which $R^9$, $R^{10}$, $R^{11}$, and $R^{12}$ independently represent a hydrogen atom or a methyl group, and n is an integer of from 1 to 5. In particular, in view of ease in availability of raw materials, price, and the like, alcohols which can be used still more advantageously are those dihydric alcohols of the formula (IV) in which $R^9$, $R^{10}$, $R^{11}$, and $R^{12}$ represent a hydrogen atom, and n is an integer of from 2 to 5.

Among these, examples of alcohols which are easily available on an industrial scale include ethylene glycol, propylene glycol, 2,3-butanediol, diethylene glycol, triethylene glycol, tetraethylene glycol, dipropylene glycol, and the like.

In the case where particularly pure raw materials do not have to be used, it is also possible to use, as their mixture, low molecular weight distribution mixtures of polyethylene glycol and polypropylene glycol (mixtures of polymers with a degree of polymerization of 10 or less).

Although the above-mentioned dihydric alcohols may be used in any amounts which may vary depending on the purpose, an effective amount is within the range of generally from 0.01 to 500 moles, practically from 0.1 to 50 moles per mole of 1,3,5-triazine derivative as a raw material from the viewpoints of reactivity and operability. When excess amounts of dihydric alcohols are used, it is possible to run the process using them also as a reaction solvent.

The metal catalyst which can be used in the present invention is preferably those catalysts which contain one or more metals selected from the group consisting of chromium, manganese, iron, cobalt, nickel, copper, niobium, molybdenum, ruthenium, rhodium, palladium, tantalum, iridium, and platinum and more preferably those catalysts which contain one or more metals selected from the group consisting of chromium, manganese, iron, nickel, copper, niobium, molybdenum, ruthenium, rhodium, palladium, tantalum, and iridium.

In particular, in view of the activity for the reaction and industrial economy, are further preferred those catalysts which contain one or more metals selected from the group, consisting of chromium, manganese, iron, nickel, copper, niobium, molybdenum, ruthenium, palladium, and tantalum.

In the present reaction, which is preferable to be conducted in heterogeneous system, it is desirable that the above-described metal catalyst is supplied usually in the form of a solid catalyst. Upon practice, the catalyst may be used either in a fluidized bed or in a fixed bed, both with good results.

The metal catalyst may be any form of the above-described metals, such as simple element, oxides, hydroxides or salts. Further, one or more metals may be used. When two or more metals are used, they can be used as a multi-element catalyst in various forms, such as alloys, intermetallic compounds, mixtures of various metal compounds. In addition to the above-described metal species, other trace metal components may also be added for highly increasing and stabilizing the catalyst activity and preventing deterioration and deactivation of the catalyst.

It is practically desirable to use the metal catalysts as a carried catalyst. In this case, generally used in industry and desirable carriers are amorphous or non-amorphous oxides of silicon, aluminum and the like, such as silica, alumina, aluminosilicate, silica-alumina, zeolite, diatomaceous earth, and clay mineral, inorganic salts such as calcium carbonate, barium carbonate, barium sulfate, and active carbon.

More specifically, examples of the catalyst include chromium oxide, manganese oxide, manganese oxide on silica, Raney iron, ferrous oxide, ferric oxide, ferric oxide on silica, Raney cobalt, cobalt oxide, Raney nickel, nickel oxide, nickel on silica, nickel on alumina, nickel on active carbon, nickel chloride,, copper oxide, niobium oxide, molybdenum oxide, molybdenum oxide on silica, ruthenium on silica, ruthenium on alumina, ruthenium on active carbon, ruthenium oxide, ruthenium black, palladium on silica, palladium on alumina, palladium on active carbon, palladium on barium sulfate, palladium on zeolite, palladium on silica-alumina, palladium chloride, palladium oxide, tantalum oxide, rhodium on silica, rhodium on alumina, rhodium on active carbon, rhodium on chloride, rhodium oxide, iridium on silica, iridium on alumina, iridium on active carbon, iridium chloride, iridium oxide, platinum on silica, platinum on alumina, platinum on active carbon, platinum chloride, platinum oxide (Adam's catalyst), platinum black, copper-chromium based catalysts, and copper-nickel based catalysts.

The catalysts described above may be used either singly or in combination as a multi-element catalyst.

The amount of the metal catalyst to be used may be in the range of normally from 0.00001 to 20 mol %, preferably from 0.0001 to 10 mol %, based on the melamine derivative of the formula (I) above.

It may be preferable to add one or more additives to the above-described catalyst before the reaction can be carried out according to the necessity. Examples of such an additive include mono- and multi-dentate tertiary phosphines, such as trimethylphosphine, triethylphosphine, tributylphosphine, triphenylphosphine, tris(paratolyl) phosphine, tris(2,6-dimethylphenyl)phosphine, sodium diphenylphosphino-benzene-3-sulfonate, bis(3-sulfonate-phenyl)phosphinobenzene sodium salt, 1,2-bis (diphenylphosphino)ethane, 1,3-bis(diphenylphosphino) propane, 1,4-bis(diphenyl-phosphino)butane, and tris(3-sulfonate-phenyl)phosphine sodium salt, phosphorous acid esters such as triethyl phosphite, tributyl phosphite, triphenyl phosphite, and tris(2,6-dimethylphenyl)phosphite, phosphonium salts such as triphenylmethylphosphonium iodide, triphenylmethylphosphonium bromide, triphenylmethylphosphonium chloride, triphenylallylphosphonium iodide, triphenylallylphosphonium bromide, triphenylallylphosphonium chloride, tetraphenylphosphonium iodide, tetraphenylphosphonium bromide, and tetraphenylphosphonium chloride, phosphoric acid esters such as triphenyl phosphate, trimethyl phosphate, triethyl phosphate, and triallyl phosphate, unsaturated hydrocarbons such as cyclooctadiene and cyclopentadiene, nitriles such as benzonitrile and acetonitrile, ketones such as acetylacetone and dibenzylidene acetone.

The amount of additive to be added may be within the range of normally from 0.01 to 10000 mol %, preferably 1 to 5000 mol %, per mol of metal catalyst.

The reaction can proceed at reaction temperatures of normally from 100° C. to 500° C., and preferred reaction temperature is 150 to 400° C. in view of the boiling point of the dihydric alcohol to be used, reactivity, reaction rate, productivity, utility, and the like.

It is desirable to set up reaction conditions so that the reaction time, which may depend on the reactivity of the melamine derivatives of the formula (I) above, can be set to usually 0.1 to 100 hours, preferably 1 to 20 hours.

The present reaction can proceed in the absence of solvents. However, solvents may be used, if desired, for improving operability or the like.

No particular limitation is posed on the solvent as far as they are inert to the reaction; for example, ethers such as tetrahydrofuran, diethyl ether, dimethoxymethane, dimethoxyethane, diethoxymethane, diethoxyethane, ethylene glycol dimethyl ether, ethylene glycol diethyl ether, ethylene glycol dibutyl ether, diethylene glycol diethyl ether, and 1,4-dioxane, aromatic hydrocarbons such as benzene, toluene, xylene, mesitylene, cumene, chlorobenzene, o-dichlorobenzene, m-dichloro-benzene, p-dichlorobenzene, and tetrahydronaphthalene, aliphatic hydrocarbons such as pentane, hexane, cyclohexane, heptane, octane, and decane, nitriles such as acetonitrile and propionitrile, esters such as methyl acetate, ethyl acetate, butyl acetate, ethyl propionate, methyl benzoate, and ethyl benzoate, amides such as N,N-dimethylformamide, N,N-dimethylacetamide, and N-methylpyrrolidone, ureas such as 1,3-dimethyl-imidazolidinone, and N,N,N',N'-tetramethylurea, and water. These may be used singly or in combination.

An excess amount of dihydric alcohols of the formula (IV) above may be used as a solvent.

The feature of the present reaction is to carry out it in a reducing atmosphere in the presence of hydrogen in the reaction system. The present inventors have found that copresence of hydrogen in the reaction system obviates the tendencies that in the absence of hydrogen, by-products are generated in large amounts upon dehydrogenation reaction of the dihydric alcohol used as a raw material and that the yield of the intended products is decreased considerably. Accordingly, the hydrogen-copresent reaction of the present invention allows the alkylation reaction to proceed preferentially for modifying only the nitrogen atom or atoms of the amino group or mono-substituted amino group on the carbon atom or atoms of 1,3,5-triazine ring, so that the conversion and recovery of the triazine derivative used can be increased to a large extent.

For the means for making hydrogen to exist in the reaction system, a method in which the reaction itself is allowed to proceed in hydrogen gas or in a hydrogen-containing gas atmosphere is desirable as a simple method.

When hydrogen gas or hydrogen-containing gases are used, the hydrogen partial pressure thereof that is preferred practically is from 0.01 to 500 kg/cm$^2$, and more preferably from 0.1 to 200 kg/cm$^2$ for industrial applications. In the case of hydrogen-containing gases, various gases can be used as a diluent gas as far as they do not participate in the reaction directly. While inert gases such as nitrogen, argon, and helium are generally used, carbon monoxide, carbon dioxide, ammonia gas, air, and the like can also be used for the purpose of stabilization of the products and catalysts as well. When the mixed gases as described above are used, there is no problem if the hydrogen partial pressure is sufficient for the reaction. It is desirable that the reaction proceed at a total pressure of from 0.1 to 500 kg/cm$^2$, preferably from 0.5 to 300 kg/cm$^2$.

When the present reaction is conductd at high temperatures, the dihydric alcohol, solvent, and the like used will generate autogenous pressures; it is desirable for practical operation to set the total pressure of the reaction system to 300 kg/cm$^2$ or less inclusive of such autogenous pressures.

As treatments after completion of the reaction, the reaction product can be under high degree of purification, and purified and isolated with ease by removing the solvent by distillation, if desired, and at this stage removing unreacted triazines by crystallization, filtration or the like means, or suitably extracting and isolating the product with the combination of organic solvent-water, and the like, and according to the necessity, by recrystallization, distillation, separation by chromatography, salt formation, and so on. The metal catalyst can be separated by filtration or the like, recovered and reused, if necessary.

The present reaction gives rise to a series of compounds with sequentially increasing degree of modification depending on the number of amino groups or substituted amino groups which can react, their reactivity, or progress of the reaction, and, hence, generally several kinds of products are obtained as a mixture and the composition of the mixture can be controlled to some extent by controlling the reaction conditions. Although for some applications of the substituted 1,3,5-triazine derivatives, the product obtained by the production method of the second invention may be used as a mixture as it is, it is also possible to separate or isolate the intended products as substances having high purity or absolutely pure substances by the above-described generally used post-treatments, if necessary, before using it.

The substituted 1,3,5-triazine derivatives, obtained by the modification method of modifying the amino group or groups on the carbon atom or atoms on the 1,3,5-triazine ring according to the second invention as described above, are 1,3,5-triazine derivatives of the formula (III)

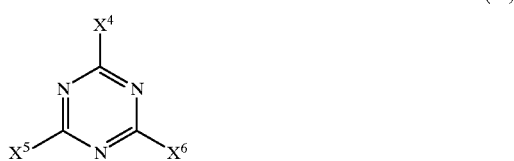
(III)

[wherein at least one of $X^4$, $X^5$ and $X^6$ independently represents an $NR^5R^6$ group {wherein at least one of $R^5$ and $R^6$ represents a substituent of the formula (V)

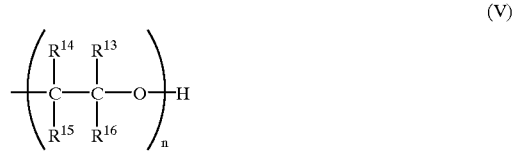
(V)

(wherein $R^{13}$, $R^{14}$, $R^{15}$, and $R^{16}$ independently represent a hydrogen atom or a $C_{1-10}$ alkyl group (wherein the alkyl group may optionally be substituted with at least one substituent selected from the group consisting of a halogen atom and a phenyl group, provided that when plural substituents are present, they may be the same or different), and n is an integer of from 1 to 10), or when either one of $R^5$ and $R^6$ is not represented by the formula (V) above, then either one of $R^5$ and $R^6$ not represented by the formula (V) above represents a hydrogen atom, a $C_{1-20}$ alkyl group (where the alkyl group may optionally be substituted with at least one substituent selected from the group consisting of a halogen atom, a $C_{1-6}$ alkoxyl group, a $C_{2-6}$ dialkylamino group, a $C_{2-7}$ alkoxycarbonyl group, and a phenyl group, provided that when plural substituents are present, they may be the same or different) or a phenyl group (where the phenyl group may optionally be substituted with at least one substituent selected from the group consisting of a halogen atom, a $C_{1-6}$ alkyl group, a $C_{1-6}$ alkoxyl group, and a $C_{1-6}$ haloalkoxyl group, provided that when plural substituents are present, they may be the same or different)}, $X^4$, $X^5$, and $X^6$ other than the $NR^5R^6$ group independently represent an $NR^7R^8$ group {wherein $R^7$ and $R^8$ independently represent a hydrogen atom, a $C_{1-20}$ alkyl group (where the alkyl group may optionally be substituted with at least one substituent selected from the group consisting of a halogen atom, a $C_{1-6}$ alkoxyl group, a $C_{2-6}$ dialkylamino group, a $C_{2-7}$ alkoxycarbonyl group, and a phenyl group, provided that when plural substituents are present, they may be the same or different) or a phenyl group (where the phenyl group may optionally be substituted with at least one substituent: selected from the group consisting of a halogen atom, a $C_{1-6}$ alkyl group, a $C_{1-6}$ alkoxyl group, and a $C_{1-6}$ haloalkoxyl group, provided that when plural substituents are present, they may be the same or different), or $R^7$ and $R^8$ together may form a 3- to 6-membered cyclic structure containing atoms freely selected from a carbon atom, an oxygen atom, and a nitrogen atom}].

Among these, preferred compounds in view of generality are substituted 1,3,5-triazine derivatives of the formula (III) in which at least one of $R^5$ and $R^6$ in the $NR^5R^6$ represents a substituent of the formula (V)

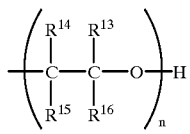

(V)

(wherein $R^{13}$, $R^{14}$, $R^{15}$, and $R^{16}$ independently represent a hydrogen atom or a $C_{1-5}$ alkyl group (wherein the alkyl group may optionally be substituted with at least one substituent selected from the group consisting of a halogen atom and a phenyl group, provided that when plural substituents are present, they may be the same or different), and n is an integer of from 1 to 5), or when either one of $R^5$ and $R^6$ is not represented by the formula (V) above, then the either one of $R^5$ and $R^6$ not represented by the formula (V) above represents a hydrogen atom, a $C_{1-20}$ alkyl group (where the alkyl group may optionally be substituted with at least one substituent selected from the group consisting of a halogen atom, a $C_{1-6}$ alkoxyl group, and a phenyl group, provided that when plural substituents are present, they may be the same or different) or a phenyl group (where the phenyl group may optionally be substituted with at least one substituent selected from the group consisting of a halogen atom, a $C_{1-6}$ alkyl group, and a $C_{1-6}$ haloalkoxyl group, provided that when plural substituents are present, they may be the same or different), $X^4$, $X^5$, and $X^6$ other than the $NR^5R^6$ group independently represent an $NR^7R^8$ group {wherein $R^7$ and $R^8$ independently represent a hydrogen atom, a $C_{1-20}$ alkyl group (where the alkyl group may optionally be substituted with at least one substituent selected from the group consisting of a halogen atom, a $C_{1-6}$ alkoxyl group, and a phenyl group, provided that when plural substituents are present, they may be the same or different) or a phenyl group (where the phenyl group may optionally be substituted with at least one substituent selected from the group consisting of a halogen atom, a $C_{1-6}$ alkyl group, and a $C_{1-6}$ haloalkoxyl group, provided that when plural substituents are present, they may be the same or different), or $R^7$ and $R^8$ together may form a 3- to 6-membered cyclic structure containing a carbon atom, an oxygen atom, and a nitrogen atom}.

Further, more preferred 1,3,5-triazine derivatives include those substituted 1,3,5-triazine derivatives of the formula (III) in which at least one of $R^5$ and $R^6$ in the $NR^5R^6$ group represents a substituent of the formula (V)

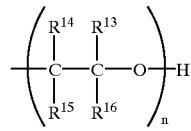

(V)

(wherein $R^{13}$, $R^{14}$, $R^{15}$, and $R^{16}$ independently represent a hydrogen atom or a methyl group and n is an integer of from 1 to 5), or when either one of $R^5$ and $R^6$ is not represented by the formula (V) above, then the either one of $R^5$ and $R^6$ not represented by the formula (V) above represents a hydrogen atom, a $C_{1-20}$ alkyl group or a phenyl group, $X^4$, $X^5$, and $X^6$ other than the $NR^5R^6$ group independently represent an $NR^7R^8$ group {wherein $R^7$ and $R^8$ independently represent a hydrogen atom, a $C_{1-20}$ alkyl group or a phenyl group, or $R^7$ and $R^8$ together may form a 3- to 6-membered cyclic structure containing atoms freely selected from a carbon atom, and a nitrogen atom}.

Further, 1,3,5-triazine derivatives which are most preferred in view of industrial and practical effects are those substituted 1,3,5-triazine derivatives of the formula (III) wherein the $R^5$ and $R^6$ in the $NR^5R^6$ group represent independently a substituent of the formula (V)

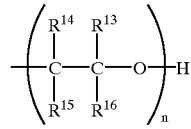

(V)

(wherein $R^{13}$, $R^{14}$, $R^{15}$, and $R^{16}$ independently represent a hydrogen atom and n is an integer of from 2 to 5), or when either one of $R^5$ and $R^6$ is not represented by the formula (V) above, then the either one of $R^5$ and $R^6$ not represented by the formula (V) above represents a hydrogen atom, $X^4$, $X^5$, and $X^6$ other than the $NR^5R^6$ group independently represent an $NR^7R^8$ group (wherein $R^7$ and $R^8$ independently represent a hydrogen atom).

As described above, in the second invention, there can be used various compounds as raw material 1,3,5-triazines and dihydric alcohols. The products obtained by the method of the present invention include various 1,3,5-triazine derivatives with various substituents depending on the combination of 1,3,5-triazine derivatives and dihydric alcohols as raw materials.

As described in the foregoing, typical examples of raw material 1,3,5-triazine derivative include melamine, various melamine derivatives, various guanamine derivatives and examples of the dihydric alcohol include diols, such as ethylene glycol and propylene glycol, derived from various petroleum chemical products and oligomers thereof, and typical products can be obtained by combining these.

While it is not intended to limit the raw materials which can be used in the present reaction to those of a specific range based on their price and ease in availability, specific examples of raw materials and substituents in products will be described below in order to further elucidate the scope of the reaction of the present invention.

Among the formulae, the substituents represented by $X^1$, $X^2$, and $X^3$ in the formula (I) for raw materials and the substituents represented by $X^4$, $X^5$, and $X^6$ in the formula (III) for products, examples of $R^1$, $R^2$, $R^3$, $R^5$, $R^6$, $R^7$, and $R^8$ on the substituents, $NHR^1$, $NR^2R^3$, $NR^5R^6$, and $NR^7R^8$, include, besides a hydrogen atom, a $C_{1-20}$ alkyl group which may be substituted, such as a methyl group, an ethyl group, an n-propyl group, an n-butyl group, an i-butyl group, a sec-butyl group, an n-amyl group, an i-amyl group, a hexyl group, a cyclohexyl group, a cyclohexylmethyl group, a heptyl group, an octyl group, a 2-ethylhexyl group, a nonyl group, a decyl group, a hexadecyl group, an octadecyl group, a trifluoromethyl group, a 3-chloropropyl group, a 2,2,2-trifluoroethyl group, a methoxymethyl group, a methoxyethyl group, an ethoxymethyl group, a cyclohexylmethoxyethyl group, an N,N-dimethylamino group, an N,N-diethylamino group, an N,N-diisopropylamino group, a methoxycarbonylmethyl group, a methoxycarbonylethyl group, a tert-butyoxycarbonylmethyl group, a cyclohexyloxycarbonylethyl group, a benzyl group, a 1-phenethyl group, and a 2-phenethyl group.

The phenyl group which may be substituted includes a phenyl group, a 2-chlorophenyl group, a 4-chlorophenyl group, a 2-fluorophenyl group, a 4-fluorophenyl group, a 2,4-dichlorophenyl group, a 2-fluoro-4-chlorophenyl group, a 2,3,4,5,6-pentafluorophenyl group, a p-tolyl group, a m-tolyl group, an o-tolyl group, a 3,5-dimethyphenyl group, a 4-cyclohexylphenyl group, a 2,4,6-trimethylphenyl group, a 2-methyl-4-isopropylphenyl group, a 3,5-dimethyoxyphenyl group, a 4-cyclopentyloxyphenyl group, a 2-trifluoromethylphenyl group, a 3-trifluoromethylphenyl group, a 4-trifluoromethylphenyl group, and the like.

The substituents of which two substituents attached to the same nitrogen atom together form a cyclic structure composed of a 3- to 6-membered ring containing atoms freely selected from a carbon atom, an oxygen atom, and a nitrogen atom include an aziridino group, an azetidino group, a pyrrolidino group, a piperidino group, a morpholino group, and the like.

Examples of the substituent having a hydroxyl group that is introduced after the reaction include a hydroxyethyl group, a 2-hydroxypropyl group, a 2-hydroxy-1-methylpropyl group, a 5-hydroxy-3-oxapentyl group, a 5-hydroxy-3-oxa-2,5-dimethylpentyl group, a 8-hydroxy-3,6-dioxaoctyl group, a 11-hydroxy-3,6,9-trioxaundecyl group, and the like. These examples of substituents are typical ones and the present invention is by no means limited thereto.

BEST MODE FOR CARRYING OUT THE INVENTION

Hereafter, the present invention will be described in further detail by examples. However, the present invention shall not be construed as being limited thereto.

In all the examples which follow, intended products were separately synthesized as specimens as shown in reference examples (the synthesis method was according to those described in J. Am. Chem. Soc., 73, p.2984 (1951), JP-A-3-215564, and U.S. Pat. No. 4,886,882), a standard curve was prepared using target compounds isolated as pure preparations and an internal standard substance, and the amounts of the intended product in the reaction mixture were determined accurately by an internal standard determination method by high performance liquid chromatography.

The analytical conditions used for high performance liquid chromatography are as follows.

(Method for determining a part of raw material triazines such as melamine and of aminotriazine after modification)

| Eluant | $CH_3CN/H_2O$ = 1/1 (v/v) |
|---|---|
| Detection method | UV 240 nm |
| | Inertsil Ph 150 mm × 4.6 mm φ, manufactured by GL Science Co., Ltd. |
| Flow rate | 1.0 ml/min. |
| Temperature for analysis | 40° C. |
| Internal standard substance | di-n-butyl phthalate |

(Method for determining a part of products and of raw materials)
By gradient analysis

| Eluant | $CH_3CN/H_2O$ = 40/60 (v/v) ↓ Gradient elution for 15 minutes $CH_3CN/H_2O$ = 1/1 (v/v) Eluted in the eluent with this composition |
|---|---|
| Detection method | UV 230 mm |
| Column | Inertsil $C_8$ 150 mm × 4.6 mm φ, manufactured by GL Science Co., Ltd. |
| Flow rate | 1.0 ml/min. |
| Temperature for analysis | 35° C. |
| Internal standard substance | di-(2-ethylhexyl) phthalate |

The 1,3,5-triazine derivatives used in the examples as araw material or obtained as a product were prepared according to the following reference examples. In addition, there were used commercially available reagents of melamine, benzoguanamine, acetoguanamine, and so on as they were. As for alcohols and metal catalysts, commercially available preparations were used as they were.

REFERENCE EXAMPLE 1

Synthesis of 2,4-diamino-6-chloro-1,3,5-triazine

To a solution obtained by dissolving 184.5 g (1.0 mol) of cyanuric chloride in 800 mL of acetonitrile at room temperature and cooling down to 0° C. was dropwise added over 2 hours 303.7 g (5.0 mol) of an aqueous 28% ammonia solution with vigorous stirring, by keeping the reaction temperature at 10° C. or lower. After completion of the dropwise addition, the cooling was discontinued and the mixture was stirred at room temperature for 1 hour, followed by gradually warming the mixture up to 45° C. and allowing the mixture to react for 4 hours. After cooling, the product was filtered and washed with a large amount of water. The filtrate was dried at 50° C. for 6 hours in vacuum to obtain 115 g (yield 79%) of the titled compound.

REFERENCE EXAMPLE 2

Synthesis of 2,4-diamino-6-butylamino-1,3,5-triazine

A mixture of 14.5 g (0.1 mol) of 2,4-diamino-6-chloro-1,3,5-triazine prepared in Reference Example 1, 100 mL of water, and 29.2 g (0.4 mol) of butylamine was warmed with stirring and allowed to react finally at a reflux temperature for 6 hours. After cooling the reaction mixture, the product was filtered and washed sufficiently with a large amount of water and then washed with toluene. The filtrate was dried at 70° C. for 6 hours in vacuum to obtain 17.5 g (yield 96%) of the titled compound. Melting point: 167° C.

REFERENCE EXAMPLE 3

Synthesis of 2,4-diamino-6-ethylamino-1,3,5-triazine

A mixed solution of 14.5 g (0.1 mol) of 2,4-diamino-6-chloro-1,3,5-triazine prepared in Reference Example 1, 12.8 g (0.2 mol) of aqueous ethylamine solution (70%), 20 mL of water, and 50 mL of 1,4-dioxane was warmed with stirring and allowed to react at a reflux temperature for 4 hours. Thereafter, a solution of 4.0 g (0.1 mol) of sodium hydroxide in 15 mL of water was dropwise added thereto over 1 hour while maintaining the reflux state. After cooling the reaction mixture, the solvent and excess ethylamine were distilled off under reduced pressure, 30 mL each of methanol and acetonitrile were added, and the unnecessary salts were filtered. To the residue obtained by distilling off the solvent from the filtered solution were added 5 mL of methanol and 40 mL of acetone to precipitate crystals, which were collected by filtration, washed with 10 mL of acetone, and dried to obtain 11.5 g (yield 75%) of the titled compound. Melting point: 171° C.

REFERENCE EXAMPLE 4

Synthesis of 2,4-diamino-6-cyclohexylamino-1,3,5-triazine

A mixed solution of 14.5 g (0.1 mol) of 2,4-diamino-6-chloro-1,3,5-triazine prepared in Reference Example 1, 140 mL of water, and 29.2 g (0.3 mol) of cyclohexylamine was warmed with stirring and allowed to react at a reflux temperature for 1 hour. Further, an aqueous solution of 12 g of sodium hydroxide in 40 mL of water was dropwise added thereto over 1 hour and the mixture was aged for 1 hour. To the reaction mixture thus obtained was added 200 mL of toluene, and the resulting mixture was cooled down to room temperature. The crystals obtained were collected by filtration, washed with 100 mL of toluene and then with 100 mL of water, followed by drying under reduced pressure to obtain 17.9 g (yield 86%) of the titled compound. Melting point: 151° C.

REFERENCE EXAMPLE 5

Synthesis of 2,4-diamino-6-piperidino-1,3,5-triazine

This was prepared according to the method of Reference Example 2. 18.4 g (yield 95%) of the compound was obtained. Melting point: 210° C.

REFERENCE EXAMPLE 6

Synthesis of 2,4-diamino-6-dodecylamino-1,3,5-triazine

This was prepared according to the method of Reference Example 2. 27.3 g (yield 94%) of the compound was obtained. Melting point: 110° C.

REFERENCE EXAMPLE 7

Synthesis of 2,4-diamino-6-octadecylamino-1,3,5-triazine

A mixed solution of 14.5 g (0.1 mol) of 2,4-diamino-6-chloro-1,3,5-triazine prepared in Reference Example 1, 60 mL of water, 60 mL of 1,4-dioxane, and 26.9 g (0.1 mol) of octadecylamine was warmed with stirring and allowed to react at a reflux temperature for 3 hours. Further, an aqueous solution of 4.0 g (0.1 mol) of sodium hydroxide in 20 mL of water was dropwise added thereto over 1 hour and the mixture was allowed to react for additional 2 hours. After cooling the reaction mixture, the solvent was distilled off under reduced pressure, and 100 mL of water and 100 mL of toluene were added to extract the product in the organic layer. After washing the organic layer with water sufficiently, the solvent was distilled off from the organic layer to obtain 34.4 g (yield 91%) of the titled compound. Melting point: 91° C.

REFERENCE EXAMPLE 8

Synthesis of 2-amino-4,6-bis(cyclohexylamino)-1,3,5-triazine

To a mixture of 18.5 g (0.1 mol) of cyanuric chloride and 50 mL of acetonitrile was added a mixed solution of 9.9 g (0.1 mol) of cyclohexlamine, 10.1 g (0.1 mol) of triethylamine and 35 mL of water over 2 hours by keeping the reaction temperature not to exceed 5° C. Thereafter, the stirring was continued for 2 hours while maintaining the temperature at 5° C. or lower. Subsequently, 70 mL of an aqueous 28% ammonia solution was dropwise added at the same temperature, followed by stirring at 5° C. for 1 hour, at 20° C. for 1 hour, and at 50° C. for 2 hours. Thereafter, 54.5 g (0.55 mol) of cyclohexylamine was dropwise added at a reaction temperature of 60° C. and the mixture was stirred at 70° C. for 3 hours. To the reaction mixture thus obtained was added 180 g of water, and the mixture was cooled down to 10° C. while continuing the stirring to precipitate crystals, which were collected by filtration, washed 5 times with 80 mL of water, and dried under reduced pressure to obtain 16.5 g (yield 57%) of the titled compound. Melting point: 153° C.

REFERENCE EXAMPLE 9

Synthesis of 2-amino-4,6-bis(n-butylamino)-1,3,5-triazine

To a mixture of 18.5 g (0.1 mol) of cyanuric chloride and 150 mL of acetonitrile was added a mixed solution of 7.3 g (0.1 mol) of n-butylamine and 20 mL of water over 2 hours by keeping the reaction temperature not to exceed 5° C. Thereafter, while maintaining the temperature at 5° C. or lower, a solution of 10.0 g (0.1 mol) of potassium hydrogen carbonate in 40 mL of water was dropwise added over 1 hour, and stirring was continued for additional 2 hours. Subsequently, 15.2 g (0.25 mol) of an aqueous 28% ammonia solution was dropwise added at the same temperature, followed by gradually elevating the temperature and stirring the mixture at 50° C. for 4 hours. Crystals were collected by filtration from the slurry solution thus obtained, washed well with water, and dried to obtain 2-amino-4-n-butylamino-6-chloro-1,3,5-triazine, as intermediate. The total amount of the crystals obtained was suspended in 100 mL of water, to which was added 8.1 g (0.11 mol) of n-butylamine, and allowed to react at a reflux temperature for 2 hours. Thereafter, a solution of 4.0 g (0.1 mol) of sodium hydroxide in 20 mL of water was dropwise added over 1 hour, and allowed to react at a reflux temperature for 2 hours. The reaction mixture was cooled and 100 mL of toluene was added thereto to extract the product, which was then washed 5 times with 80 mL of water. The solvent was distilled off from the organic layer thus obtained under reduced pressure to obtain 27.0 g (yield 92%) of the titled compound. Melting point: 73° C.

REFERENCE EXAMPLE 10

Synthesis of 2,4,6-tris(butylamino)-1,3,5-triazine

To a solution of 18.5 g (0.1 mol) of cyanuric chloride in 150 mL of acetonitrile cooled to 0° C. was dropwise added a solution of 14.6 g (0.2 mol) of butylamine in 20 mL of water over 1 hour with stirring by keeping the reaction temperature not to exceed 5° C. Further, while continuing the stirring, a solution of 20.0 g (0.2 mol) of potassium hydrogen carbonate in 100 mL of water was dropwise added at the same temperature. Thereafter, the reaction temperature was gradually elevated and the stirring was continued at 45° C. for 8 hours. After confirming the completion of conversion to 2,4-bis(butylamino)-6-chloro-1,3,5-triazine by high performance liquid chromatography, the reaction mixture was cooled and the product was separated by filtration. The filtration cake was washed well with a large amount of water and this 2,4-bis(butylamino)-6-chloro-1,3,5-triazine was suspended in 100 mL of water. To the suspension was added 29.2 g (0.4 mol) of butylamine and allowed to react by heating under reflux for 6 hours. After cooling, 200 mL of toluene was added and the mixture was stirred vigorously, followed by separation of the aqueous layer. Further, the toluene layer was washed three times with 150 mL of water. Subsequently, toluene in the organic layer was distilled off by heating under reduced pressure to obtain 28.2 g (yield 96%) of the titled compound. Propery: oily product

REFERENCE EXAMPLE 11

Synthesis of 2,4,6-tris(cyclohexylamino)-1,3,5-triazine

To a solution of 18.5 g (0.1 mol) of cyanuric chloride dissolved in 350 mL of 1,4-dioxane was dropwise added, over 1 hour, 59.4 g (0.6 mol) of cyclohexylamine while stirring the solution warmed to 50° C. and maintaining the reaction temperature at 50° C. The reaction temperature was elevated while continuing the stirring and then 59.4 g (0.6 mol) of cyclohexylamine was dropwise added again at a reaction temperature of 85° C. After continuing the reaction for 6 hours with elevating the reaction temperature under reflux, 250 mL of water was dropwise added at the same temperature and the mixture was cooled down to room temperature while continuing the stirring. Crystals which precipitated were collected by filtration, washed four times with 150 mL of water, dried under reduced pressure to obtain 34.0. g (yield 91%) of the titled compound. Melting point: 225° C.

REFERENCE EXAMPLE 12

Synthesis of 2,4,6-tris(ethylamino)-1,3,5-triazine

Synthesis was carried out acording to the method of Reference Example 10 to obtain 20.0 g (yield 95%) of the titled compound. Melting point: 74° C.

REFERENCE EXAMPLE 13

Synthesis of 2,4,6-tris(2-ethylhexylamino)-1,3,5-triazine

Synthesis was carried out according to the method of Reference Example 10 to obtain 41.6 g (yield 90%) of the titled compound. Property: paste

REFERENCE EXAMPLE 14

Synthesis of 2,4-diamino-6-(2-ethylhexylamino)-1,3,5-triazine

Synthesis was carried out according to the method of Reference Example 2 except that 12.9 g (0.1 mol) of 2-ethylhexylamine was used. The amount of the titled compound obtained was 18.6 g (yield 78%). Melting point: 81° C.

REFERENCE EXAMPLE 15

Synthesis of 2,4-diamino-6-(5-hydroxy-3-oxapentylamino)-1,3,5-triazine 14.5 g (0.1 mol) of 2,4-diamino-6-chloro-1,3,5-triazine and 11.6 g (0.11 mol) of 2-(2'-aminoethoxy)ethanol were added to 60 mL of water and heated to 100° C. while stirring the mixture as a suspension. After continuing the reaction for 2 hours, an aqueous solution of 4.0 g (0.1 mol) of sodium hydroxide in 20 mL of water was dropwise added over 1 hour while maintaining the reaction temperature, and the reaction was continued for further 3 hours at the same temperature. The homogeneous reaction mixture thus obtained was gradually cooled and allowed to stand at room temperature for one night. The crystals precipitated were collected by filtration, washed with a small amount of water, and recrystallized from water to obtain 13.5 g of the intended compound, 2,4-diamino-6-(5-hydroxy-3-oxapentylamino)-1,3,5-triazine as crystals. Yield 62%.

REFERENCE EXAMPLE 16

Synthesis of 2-amino-4,6-bis(5-hydroxy-3-oxapentylamino)-1,3,5-triazine 18. 5 g (0.1 mol) of cyanuric chloride was added to 100 mL of acetonitrile and cooled down to 0° C. While stirring, 10.5 g (0.1 mol) of 2-(2'-aminoethoxy)ethanol was dropwise added over 1 hour by keeping the reaction temperature not to exceed 5° C. and the mixture was further stirred at 5° C. or lower for 2 hours. Subsequently, a solution of 10.0 g (0.1 mol) of potassium hydrogen carbonate in 70 mL of water was dropwise added over 2 hours at the same temperature, the cooling was discontinued, and the stirring was continued until the temperature reached room temperature (25° C.). Thereafter, 24.3 g (0.4 mol) of an aqueous 28% ammonia solution was gradually added at room temperature, followed by warming and the mixture was stirred at 40 to 45° C. for 4 hours for reaction. The reaction mixture was concentrated at 50° C. or lower under reduced pressure to half the original volume. To the mixture thus obtained was added 10.5 g (0.1 mol) of 2-(2'-aminoethoxy)ethanol, and heated to elevate the temperature to 100° C. After continuing the reaction for 2 hours, an aqueous solution of 4.0 g (0.1 mol) of sodium hydroxide in 20 mL of water was dropwise added over 1 hour while maintaining the reation temperature, and the reaction was continued for further 3 hours at the same temperature. The homogeneous reaction mixture thus obtained was concentrated to dryness under reduced pressure, and then 100 mL of ethanol was added thereto, the insoluble matter being separated by filtration. After concentrating the filtered solution to dryness, 100 mL of isopropyl alcohol was added and the same procedures were repeated. The viscous mixture thus obtained was separated purified by silica gel column chromatography (eluant: ethyl acetate/ethanol=1/1) toobtain 25.7 g of the intended compound, 2-amino-4,6-bis(5-hydroxy-3-oxapentylamino)-1,3,5-triazine as viscous product. Yield 85%

EXAMPLE 1

Reaction of Melamine with Ethanol

In a stainless steel autoclave having an inner volume of 70 mL were charged 1.26 g (0.01 mol) of melamine (2,4,6- triamino-1,3,5-triazine), 25 mg of 5% Pd-C catalyst (water content 50%), and 30 mL of ethanol, and after purging the inside of the reaction system sufficiently with nitrogen, 10 kg/cm$^2$ of hydrogen gas was introduced at room temperature. The temperature was elevated while stirring, the reaction was carried out at a reaction temperature of 210° C. for 2 hours, followed by cooling, and the contents were quantitatively analyzed. As a result, the conversion of melamine, raw material, was 11.0%, and the products were 2,4-diamino-6-ethylamino-1,3,5-triazine in a yield of 9.1% and 2-amino-4,6-bis(ethylamino)-1,3,5-triazine in a yield of 1.2%.

EXAMPLE 2

Reaction of Melamine with Ethanol

The same reaction and post-treatments as in Example 1 were carried out except that the reaction temperature was changed to 240° C. and the reaction time was changed to 1.5 hours, and as a result, the conversion of melamine, raw material, was 25.1%, and the products were 2,4-diamino-6-ethylamino-1,3,5-triazine in a yield of 22.0%, 2-amino-4,6-bis(ethylamino)-1,3,5-triazine in a yield of 2.2% and 2,4,6-tris(ethylamino)-1,3,5-triazine in a yield of 0.5%.

EXAMPLE 3

Reaction of Melamine with 1-butanol

In a stainless steel autoclave having an inner volume of 70 mL were charged 1.26 g (0.01 mol) of melamine, 25 mg of 5% Pd-C catalyst (water content 50%), and 30 mL of butanol, and after purging the inside of the reaction system sufficiently with nitrogen, 40 kg/cm$^2$ of hydrogen gas was introduced. The temperature was elevated while stirring, the reaction was carried out at a reaction temperature of 240° C. for 2 hours, followed by cooling, and the contents were quantitatively analyzed. As a result, the conversion of melamine, raw material, was 13.3%, and the products were 2,4-diamino-6-butylamino-1,3,5-triazine in a yield of 11.2% and 2-amino-4,6-bis(butylamino)-1,3,5-triazine in a yield of 1.5%.

EXAMPLE 4

Reaction of Melamine with 1-butanol

The same reaction and post-treatments as in Example 3 were carried out except that the hydrogen gas pressure was changed to 10 kg/cm$^2$, and as a result, the conversion of melamine, raw material, was 16.3%, and the products were 2,4-diamino-6-butylamino-1,3,5-triazine in a yield of 13.1% and 2-amino-4,6-bis(butylamino)-1,3,5-triazine in a yield of 1.9%.

EXAMPLE 5

Reaction of Melamine with 1-butanol

In a stainless steel autoclave having an inner volume of 70 mL were charged 1.26 g (0.01 mol) of melamine, 25 mg of 5% Pd-C catalyst (water content 50%), and 30 mL of butanol, and after purging the inside of the reaction system sufficiently with nitrogen, gas exchange was performed 5 times with 10 kg/cm$^2$ of hydrogen gas. Then, the pressure was reduced to a residual hydrogen pressure of 5 kg/cm$^2$. The temperature was elevated while stirring, the reaction was carried out at a reaction temperature of 240° C. for 3 hours, followed by cooling, and the contents were quantitatively analyzed. As a result, the conversion of melamine, raw material, was 43.1%, and the products were 2,4-diamino-6-butylamino-1,3,5-triazine in a yield of 36.8%, 2-amino-4,6-bis(butylamino)-1,3,5-triazine in a yield of 5.0%, and 2,4,6-tris(butylamino)-1,3,5-triazine in a yield of 0.8%. The recovery of the product as compared with the conversion of raw material was 98.8%.

EXAMPLE 6

Reaction of Melamine with 1-butanol

The same reaction and post-treatments as in Example 4 were carried out except that the reaction temperature was changed to 260° C. As a result, the conversion of melamine, raw material, was 68.9%, and the products were 2,4-diamino-6-butylamino-1,3,5-triazine in a yield of 44.5%, 2-amino-4,6-bis(butylamino)-1,3,5-triazine in a yield of 19.2%, and 2,4,6-tris(butylamino)-1,3,5-triazine in a yield of 3.3%.

EXAMPLE 7

Reaction of Melamine with 1-butanol

The same reaction and post-treatments as in Example 6 were carried out except that the reaction time was changed to 5 hours. As a result, the conversion of melamine, raw material, was 97.8%, and the products were 2,4-diamino-6-butylamino-1,3,5-triazine in a yield of 22.5%, 2-amino-4,6-bis(butylamino)-1,3,5-triazine in a yield of 47.6%, and 2,4,6-tris(butylamino)-1,3,5-triazine in a yield of 25.0%, and 2,4-bis(butylamino)-6-dibutylamino-1,3,5-triazinein a yield of 1.3%.

EXAMPLE 8

Reaction of Melamine with 1-butanol

The same reaction and post-treatments as in Example 4 were carried out except that the reaction temperature was changed to 280° C. As a result, the conversion of melamine, raw material, was 94.9%, and the products were 2,4-diamino-6-butylamino-1,3,5-triazine in a yield of 32.5%, 2-amino-4,6-bis(butylamino)-1,3,5-triazine in a yield of 45.2%, and 2,4,6-tris(butylamino)-1,3,5-triazine in a yield of 14.3%, and 2,4-bis(butylamino)-6-dibutylamino-1,3,5-triazine in a yield of 1.2%.

EXAMPLE 9

Reaction of Melamine with Cyclohexanol

In a stainless steel autoclave having an inner volume of 70 mL were charged 1.26 g (0.01 mol) of melamine, 25 mg of 5% Pd-C catalyst (water content 50%), and 30 mL of cyclohexanol, and after purging the inside of the reaction system sufficiently with nitrogen, gas exchange was performed 5 times with 10 kg/cm$^2$ of hydrogen gas. While keeping 10 kg/cm$^2$ of hydrogen in the reactor, the temperature was elevated with stirring, the reaction was carried out at a reaction temperature of 260° C. for 2 hours, followed by cooling, and the contents were quantitatively analyzed. As a result, the conversion of melamine, raw material, was 15.5%, and the products were 2,4-diamino-6-cyclohexylamino-1,3,5-triazine in a yield of 13.7% and 2-amino-4,6-bis(cyclohexylamino)-1,3,5-triazine in a yield of 1.6%.

EXAMPLE 10

Reaction of Melamine with Cyclohexanol

In a stainless steel autoclave having an inner volume of 70 mL were charged 1.26 g (0.01 mol) of melamine, 25 mg of 5% Pd-C catalyst (water content 50%), and 30 mL of cyclohexanol, and after purging the inside of the reaction system sufficiently with nitrogen, gas exchange was performed 5 times with 10 kg/cm$^2$ of hydrogen gas. While keeping 10 kg/cm$^2$ of hydrogen in the reactor, the temperature was elevated with stirring, the reaction was carried out at a reaction temperature of 280° C. for 5 hours, followed by cooling, and the contents were quantitatively analyzed. As a result, the conversion of melamine, raw material, was 67.6%, and the products were 2,4-diamino-6-cyclohexylamino-1,3,5-triazine in a yield of 48.3%, 2-amino-4,6-bis(cyclohexylamino)-1,3,5-triazine in a yield of 14.1%, and 2,4,6-tris(cyclohexylamino)-1,3,5-triazine in a yield of 4.5%.

EXAMPLE 11

Reaction of Melamine with 2-ethylhexanol

In a stainless steel autoclave having an inner volume of 70 mL were charged 1.26 g (0.01 mol) of melamine, 25 mg of 5% Pd-C catalyst (water content 50%), and 30 mL of 2-ethylhexanol, and after purging the inside of the reaction system sufficiently with nitrogen, gas exchange was performed 5 times with 10 kg/cm$^2$ of hydrogen gas. While retaining hydrogen in the reactor, the temperature was elevated with stirring, the reaction was carried out at a reaction temperature of 240° C. for 2 hours, followed by cooling, and the contents were quantitatively analyzed. As a result, the conversion of melamine, raw material, was 5.3%, and the products were 2,4-diamino-6-(2-ethylhexylamino)-1,3,5-triazine in a yield of 4.9% and 2-amino-4,6-bis(2-ethylhexylamino)-1,3,5-triazine in a yield of 0.2%.

EXAMPLE 12

Reaction of Melamine with 2-ethylhexanol

In a stainless steel autoclave having an inner volume of 70 mL were charged 1.26 g (0.01 mol) of melamine, 25 mg of 5% Pd-C catalyst (water content 50%), and 30 mL of 2-ethylhexanol, and after purging the inside of the reaction system sufficiently with nitrogen, gas exchange was performed 5 times with 10 kg/cm$^2$ of hydrogen gas. While retaining hydrogen in the reactor, the temperature was elevated with stirring, the reaction was carried out at a reaction temperature of 280° C. for 6 hours, followed by cooling, and the contents were quantitatively analyzed. As a result, the conversion of melamine, raw material, was 55.3%, and the products were 2,4-diamino-6-(2-ethylhexylamino)-1,3,5-triazine in a yield of 36.2%, 2-amino-4,6-bis(2-ethylhexylamino)-1,3,5-triazine in a yield of 16.1%, and 2,4,6-tris(2-cyclohexylamino)-1,3,5-triazine in a yield of 2.1%.

EXAMPLE 13

Reaction of Melamine with 1-butanol

In a stainless steel autoclave having an inner volume of 70 mL were charged 1.26 g (0.01 mol) of melamine, 12.5 mg of 5% Ru on active carbon catalyst, and 30 mL of butanol, and after purging the inside of the reaction system sufficiently with nitrogen, 10 kg/cm of hydrogen gas was introduced. The temperature was elevated while stirring, the reaction was carried out at a reaction temperature of 240° C. for 2 hours, followed by cooling, and the contents were quantitatively analyzed. As a result, the conversion of melamine, raw material, was 14.2%, and the products were 2,4-diamino-6-butylamino-1,3,5-triazine in a yield of 8.2% and 2-amino-4,6-bis(butylamino)-1,3,5-triazine in a yield of 1.6%.

EXAMPLE 14

Reaction of Melamine with 1-butanol

In a stainless steel autoclave having an inner volume of 70 mL were charged 1.26 g (0.01 mol) of melamine, 25.0 mg of 5% Pd-5% Cu on active carbon catalyst, and 30 mL of butanol, and after purging the inside of the reaction system sufficiently with nitrogen, 10 kg/cm$^2$ of hydrogen gas was introduced. The temperature was elevated while stirring, the reaction was carried out at a reaction temperature of 240° C. for 3 hours, followed by cooling, and the contents were quantitatively analyzed. As a result, the conversion of melamine, raw material, was 18.6%, and the products were 2,4-diamino-6-butylamino-1,3,5-triazine in a yield of 14.7% and 2-amino-4,6-bis(butylamino)-1,3,5-triazine in a yield of 3.2%.

EXAMPLE 15

Reaction of Melamine with 1-butanol

In a stainless steel autoclave having an inner volume of 70 mL were charged 1.26 g (0.01 mol) of melamine, 25.0 mg of 2% Pt on active carbon catalyst, and 30 mL of butanol, and after purging the inside of the reaction system sufficiently with nitrogen, 10 kg/cm$^2$ of hydrogen gas was introduced. The temperature was elevated while stirring, the reaction was carried out at a reaction temperature of 240° C. for 1 hour, followed by cooling, and the contents were quantitatively analyzed. As a result, the conversion of melamine, raw material, was 5.8%, and the products were 2,4-diamino-6-butylamino-1,3,5-triazine in a yield of 4.1% and 2-amino-4,6-bis(butylamino)-1,3,5-triazine in a yield of 1.1%.

EXAMPLE 16

Reaction of Melamine with 1-butanol

In a stainless steel autoclave having an inner volume of 70 mL were charged 1.26 g (0.01 mol) of melamine, 25.0 mg of copper-chromite catalyst (manufactured by NISSAN GIRDLER CATALYST CO., LTD., copper 36% by weight, chromium 32% by weight), and 30 mL of butanol, and after purging the inside of the reaction system sufficiently with nitrogen, 10 kg/cm$^2$ of hydrogen gas was introduced. The temperature was elevated while stirring, the reaction was carried out at a reaction temperature of 240° C. for 1 hour, followed by cooling, and the contents were quantitatively analyzed. As a result, the conversion of melamine, raw material, was 3.4%, and the products were 2,4-diamino-6-butylamino-1,3,5-triazine in a yield of 3.0% and 2-amino-4,6-bis(butylamino)-1,3,5-triazine in a yield of a trace amount.

EXAMPLE 17

Reaction of Melamine with 1-butanol

In a stainless steel autoclave having an inner volume of 70 mL were charged 1.26 g (0.01 mol) of melamine, 25.0 mg of Raney nickel catalyst (nickel content 41% by weight, iron content 0.5% by weight, manufactured by KAWAKEN FINE CHEMICAL CO., LTD.), and 30 mL of butanol, and after purging the inside of the reaction system sufficiently with nitrogen, 10 kg/cm$^2$ of hydrogen gas was introduced. The temperature was elevated while stirring, the reaction was carried out at a reaction temperature of 240° C. for 1 hour, followed by cooling, and the contents were quantitatively analyzed. As a result, the conversion of melamine, raw material, was 6.1%, and the products were 2,4-diamino-6-butylamino-1,3,5-triazine in a yield of 5.5% and 2-amino-4,6-bis(butylamino)-1,3,5-triazine in a yield of a trace amount.

EXAMPLE 18

Reaction of Melamine with 1-butanol

In a stainless steel autoclave having an inner volume of 70 mL were charged 1.26 g (0.01 mol) of melamine, 25.0 mg of Raney cobalt catalyst (cobalt content 50% by weight, manufactured by KAWAKEN FINE CHEMICAL CO., LTD.), and 30 mL of butanol, and after purging the inside of the reaction system sufficiently with nitrogen, 10 kg/cm$^2$ of hydrogen gas was introduced. The temperature was elevated while stirring, the reaction was carried out at a reaction temperature of 240° C. for 1 hour, followed by cooling, and the contents were quantitatively analyzed. As a result, the conversion of melamine, raw material, was 5.4%, and the products were 2,4-diamino-6-butylamino-1,3,5-triazine in a yield of 4.7%.

EXAMPLE 19

Reaction of Melamine with 1-butanol

In a stainless steel autoclave having an inner volume of 70 mL were charged 1.26 g (0.01 mol) of melamine, 12.5 mg of Raney nickel catalyst (nickel content 41% by weight, iron content 0.5% by weight, manufactured by KAWAKEN FINE CHEMICAL CO., LTD.), Raney copper catalyst (copper content 50% by weight, manufactured by KAWAKEN FINE CHEMICAL CO., LTD.), and 30 mL of butanol, and after purging the inside of the reaction system sufficiently with nitrogen, 10 kg/cm$^2$ of hydrogen gas was introduced. The temperature was elevated while stirring, the reaction was carried out at a reaction temperature of 240° C. for 1 hour, followed by cooling, and the contents were quantitatively analyzed. As a result, the conversion of melamine, raw material, was 7.8%, and the products were 2,4-diamino-6-butylamino-1,3,5-triazine in a yield of 5.5% and 2-amino-4,6-bis(butylamino)-1,3,5-triazine in a yield of 1.6%.

EXAMPLE 20

Reaction of Melamine with 1-butanol

In a stainless steel autoclave having an inner volume of 70 mL were charged 1.26 g (0.01 mol) of melamine, 25.0 mg of 5% Pd on alumina catalyst, and 30 mL of butanol, and after purging the inside of the reaction system sufficiently with nitrogen, 10 kg/cm$^2$ of hydrogen gas was introduced. The temperature was elevated while stirring, the reaction was carried out at a reaction temperature of 260° C. for 3 hours, followed by cooling, and the contents were quantitatively analyzed. As a result, the conversion of melamine, raw material, was 71.7%, and the products were 2,4-diamino-6-butylamino-1,3,5-triazine in a yield of 41.6%, 2-amino-4,6-bis(butylamino)-1,3,5-triazine in a yield of 25.3%, and 2,4,6-tris(butylamino)-1,3,5-triazine in a yield of 3.4%.

EXAMPLE 21

Reaction of Melamine with 1-butanol

In a stainless steel autoclave having an inner volume of 70 mL were charged 1.26 g (0.01 mol) of melamine, 50.0 mg of 2% Pd on Y type zeolite catalyst, and 30 mL of butanol, and after purging the inside of the reaction system sufficiently with nitrogen, 10 kg/cm$^2$ of hydrogen gas was introduced. The temperature was elevated while stirring, the reaction was carried out at a reaction temperature of 260° C. for 6 hours, followed by cooling, and the contents were quantitatively analyzed. As a result, the conversion of melamine, raw material, was 51.8%, and the products were 2,4-diamino-6-butylamino-1,3,5-triazine in a yield of 42.1%, 2-amino-4,6-bis(butylamino)-1,3,5-triazine in a yield of 7.7%, and 2,4,6-tris(butylamino)-1,3,5-triazine in a yield of 1.5%.

EXAMPLE 22

Reaction of Melamine with 1-butanol

In a stainless steel autoclave having an inner volume of 70 mL were charged 1.26 g (0.01 mol) of melamine, 25.0 mg of 5% Pd on calcium carbonate catalyst, and 30 mL of butanol, and after purging the inside of the reaction system sufficiently with nitrogen, 10 kg/cm$^2$ of hydrogen gas was introduced. The temperature was elevated while stirring, the reaction was carried out at a reaction temperature of 260° C. for 5 hours, followed by cooling, and the contents were quantitatively analyzed. As a result, the conversion of melamine, raw material, was 66.9%, and the products were 2,4-diamino-6-butylamino-1,3,5-triazine in a yield of 44.5%, 2-amino-4,6-bis(butylamino)-1,3,5-triazine in a yield of 16.4%, and 2,4,6-tris(butylamino)-1,3,5-triazine in a yield of 4.1%.

EXAMPLE 23

Reaction of Melamine with 1-butanol

In a stainless steel autoclave having an inner volume of 70 mL were charged 1.26 g (0.01 mol) of melamine, 25.0 mg of Ni/NiO on silica catalyst, and 30 mL of butanol, and after purging the inside of the reaction system sufficiently with nitrogen, 10 kg/cm$^2$ of hydrogen gas was introduced. The temperature was elevated while stirring, the reaction was carried out at a reaction temperature of 260° C. for 3 hours, followed by cooling, and the contents were quantitatively analyzed. As a result, the conversion of melamine, raw material, was 65.7%, and the products were 2,4-diamino-6-butylamino-1,3,5-triazine in a yield of 40.6%, 2-amino-4,6-bis(butylamino)-1,3,5-triazine in a yield of 19.3%, and 2,4,6-tris(butylamino)-1,3,5-triazine in a yield of 4.6%.

EXAMPLE 24

Reaction of 2,4-diamino-6-ethylamino-1,3,5-triazine with Ethanol

In a stainless steel autoclave having an inner volume of 70 mL were charged 1.54 g (0.01 mol) of 2,4-diamino-6-ethylamino-1,3,5-triazine, 25 mg of 5% Pd-C on active carbon catalyst, and 30 mL of ethanol, and after purging the inside of the reaction system sufficiently with nitrogen, gas exchange was performed 5 times with 10 kg/cm$^2$ of hydrogen gas. While retaining hydrogen pressure in the reactor, the temperature was elevated with stirring, the reaction was carried out at a reaction temperature of 260° C. for 4 hours, followed by cooling, and the contents were quantitatively analyzed. As a result, the conversion of 2,4-diamino-6-ethylamino-1,3,5-triazine, raw material, was 81.4%, and the products were 2-amino-4,6-bis(ethylamino)-1,3,5-triazine in a yield of 50.8%, 2,4,6-tris(ethylamino)-1,3,5-triazine in a yield of 18.7%, 2-diethylamino-4,6-bis(ethylamino)-1,3,5-triazine in a yield of 8.8%, and 2,4-bis(diethylamino)-6-ethylamino-1,3,5-triazine in a yield of 2.2%.

EXAMPLE 25

Reaction of 2,4-diamino-6-butylamino-1,3,5-triazine with 1-butanol

In a stainless steel autoclave having an inner volume of 70 mL were charged 1.82 g (0.01 mol) of 2,4-diamino-6-butylamino-1,3,5-triazine, 25 mg of 5% Pd-C catalyst (water content 50%), and 30 mL of butanol, and after purging the inside of the reaction system sufficiently with nitrogen, 10 kg/cm$^2$ of hydrogen gas was introduced. While retaining the hydrogen pressure in the reactor, the temperature was elevated with stirring, the reaction was carried out at a reaction temperature of 260° C. for 2 hours, followed by cooling, and the contents were quantitatively analyzed. As a result, the conversion of 2,4-diamino-6-butylamino-1,3,5-triazine, raw material, was 78.5%, and the products were 2-amino-4,6-bis(butylamino)-1,3,5-triazine in a yield of 51.2%, 2,4,6-tris(butylamino)-1,3,5-triazine in a yield of 23.8%, and 2-dibutylamino-4,6-bis(butylamino)-1,3,5-triazine in a yield of 2.9%.

EXAMPLE 26

Reaction of 2-amino-4,6-bis(butylamino)-1,3,5-triazine with 1-butanol

In a stainless steel autoclave having an inner volume of 70 mL were charged 2.38 g (0.01 mol) of 2-amino-4,6-bis(butylamino)-1,3,5-triazine, 25 mg of 5% Pd-C catalyst (water content 50%), and 30 mL of butanol, and after purging the inside of the reaction system sufficiently with nitrogen, 7 kg/cm$^2$ of hydrogen gas was introduced. The temperature was elevated with stirring, the reaction was carried out at a reaction temperature of 260° C. for 2 hours, followed by cooling, and the contents were quantitatively analyzed. As a result, the conversion of 2-amino-4,6-bis(butylamino)-1,3,5-triazine, raw material, was 47.1%, and the products were 2,4,6-tris(butylamino)-1,3,5-triazine in a yield of 41.2%, 2,4-bis(butylamino)-6-dibutylamino-1,3,5-triazine in a yield of 3.2%, and 2-butylamino-4,6-bis(dibutylamino)-1,3,5-triazine in a yield of 2.2%.

EXAMPLE 27

Reaction of 2,4,6-tris(butylamino)-1,3,5-triazine with 1-butanol

In a stainless steel autoclave having an inner volume of 70 mL were charged 2.94 g (0.01 mol) of 2,4,6-tris(butylamino)-1,3,5-triazine, 25 mg of 5% Pd-C catalyst (water content 50%), and 30 mL of butanol, and after purging the inside of the reaction system sufficiently with nitrogen, 10 kg/cm$^2$ of hydrogen gas was introduced. The temperature was elevated with stirring, the reaction was carried out at a reaction temperature of 260° C., for 3 hours, followed by cooling, and the contents were quantitatively analyzed. As a result, the conversion of 2,4,6-tris(butylamino)-1,3,5-triazine, raw material, was 15.8%, and the products were 2,4-bis(butylamino)-6-dibutylamino-1,3,5-triazine in a yield of 10.7%, 2-butylamino-4,6-bis(dibutylamino)-1,3,5-triazine in a yield of 3.7%, and 2,4,6-tris(dibutylamino)-1,3,5-triazine in a yield of 0.7%.

EXAMPLE 28

Reaction of 2,4-diamino-6-cyclohexylamino-1,3,5-triazine with Cyclohexanol

In a stainless steel autoclave having an inner volume of 70 mL were charged 2.08 g (0.01 mol) of 2,4-diamino-6-cyclohexylamino-1,3,5-triazine, 25 mg of 5% Pd-C catalyst (water content 50%), and 30 mL of cyclohexanol, and after purging the inside of the reaction system sufficiently with nitrogen, 10 kg/cm$^2$ of hydrogen gas was introduced. The temperature was elevated with stirring, the reaction was carried out at a reaction temperature of 270° C. for 4 hours, followed by cooling, and the contents were quantitatively analyzed. As a result, the conversion of 2,4-diamino-6-cyclohexylamino-1,3,5-triazine, raw material, was 28.3%, and the products were 2-amino-4,6-bis(cyclohexylamino)-1,3,5-triazine in a yield of 23.1%, 2,4,6-tris(cyclohexylamino)-1,3,5-triazine in a yield of 4.9%.

EXAMPLE 29

Reaction of 2,4-diamino-6-dodecylamino-1,3,5-triazine with 1-butanol

In a stainless steel autoclave having an inner volume of 70 mL were charged 2.94 g (0.01 mol) of 2,4-diamino-6-dodecylamino-1,3,5-triazine, 25 mg of 5% Pd-C catalyst (water content 50%), and 30 mL of butanol, and after purging the inside of the reaction system sufficiently with nitrogen, 10 kg/cm$^2$ of hydrogen gas was introduced. The temperature was elevated with stirring, the reaction was carried out at a reaction temperature of 260° C. for 4 hours, followed by cooling, and the contents were quantitatively analyzed. As a result, the conversion of 2,4-diamino-6-dodecylamino-1,3,5-triazine, raw material, was 65.2%, and the products were 2-amino-4-butylamino-6-dodecylamino-1,3,5-triazine in a yield of 45.1%, 2,4-bis(butylamino)-6-dodecylamino-1,3,5-triazine in a yield of 17.7%, and a 2-butylamino-4-dibutylamino-6-dodecylamino-1,3,5-triazine in a yield of 1.3%.

EXAMPLE 30

Reaction of 2,4-diamino-6-dodecylamino-1,3,5-triazine with 1-butanol

In a stainless steel autoclave having an inner volume of 70 mL were charged 3.78 g (0.01 mol) of 2,4-diamino-6-octadecylamino-1,3,5-triazine, 25 mg of 5% Pd-C catalyst (water content 50%), and 30 mL of butanol, and after purging the inside of the reaction system sufficiently with nitrogen, 10 kg/cm$^2$ of hydrogen gas was introduced. The temperature was elevated with stirring, the reaction was carried out at a reaction temperature of 260 for 4 hours, followed by cooling, and the contents were quantitatively analyzed. As a result, the conversion of 2,4-diamino-6-dodecylamino-1,3,5-triazine, raw material, was 61.6%, and the products were 2-amino-4-butylamino-6-octadecylamino-1,3,5-triazine in a yield of 41.4%, 2,4-bis(butylamino)-6-octadecylamino-1,3,5-triazine in a yield of 17.5%, and a 2-butylamino-4-dibutylamino-6-octadecylamino-1,3,5-triazine in a yield of a trace amount.

EXAMPLE 31

Reaction of 2,4-diamino-6-piperidino-1,3,5-triazine with 1-butanol

In a stainless steel autoclave having an inner volume of 70 mL were charged 1.94 g (0.01 mol) of 2,4-diamino-6-piperidino-1,3,5-triazine, 25 mg of 5% Pd-C catalyst (water content 50%), and 30 mL of butanol, and after purging the inside of the reaction system sufficiently with nitrogen, 10 kg/cm$^2$ of hydrogen gas was introduced. The temperature was elevated with stirring, the reaction was carried out at a reaction temperature of 260° C. for 5 hours, followed by cooling, and the contents were quantitatively analyzed. As a result, the conversion of 2,4-diamino-6-piperidino-1,3,5-triazine, raw material, was 76.8%, and the products were 2-amino-4-butylamino-6-piperidino-1,3,5-triazine in a yield of 52.7%, 2,4-bis(butylamino)-6-piperidino-1,3,5-triazine in a yield of 22.6%, and a 2-butylamino-4-dibutylamino-6-piperidino-1,3,5-triazine in a yield of a trace amount.

EXAMPLE 32

Reaction of Benzoguanamine with 1-butanol

In a stainless steel autoclave having an inner volume of 70 mL were charged 1.87 g (0.01 mol) of benzoguanamine (2,4-diamino-6-phenyl-1,3,5-triazine), 25 mg of 5% Pd-C catalyst (water content 50%), and 30 mL of butanol, and after purging the inside of the reaction system sufficiently with nitrogen, 10 kg/cm$^2$ of hydrogen gas was introduced. The temperature was elevated with stirring, the reaction was carried out at a reaction temperature of 240° C. for 2 hours, followed by cooling, and the contents were quantitatively analyzed. As a result, the conversion of benzoguanamine, raw material, was 36.7%, and the products were 2-amino-4-butylamino-6-phenyl-1,3,5-triazine in a yield of 29.7% and 2,4-bis(butylamino)-6-phenyl-1,3,5-triazine in a yield of 6.5%.

EXAMPLE 33

Reaction of Acetoguanamine with Ethanol

In a stainless steel autoclave having an inner volume of 70 mL were charged 1.25 g (0.01 mol) of acetoguanamine (2,4-diamino-6-methyl-1,3,5-triazine), 25 mg of 5% Pd-C catalyst (water content 50%), and 30 mL of ethanol, and after purging the inside of the reaction system sufficiently with nitrogen, 10 kg/cm$^2$ of hydrogen gas was introduced. The temperature was elevated with stirring, the reaction was carried out at a reaction temperature of 240° C. for 3 hours, followed by cooling, and the contents were quantitatively analyzed. As a result, the conversion of acetoguanamine, raw material, was 47.2%, and the products were 2-amino-4-ethylamino-6-methyl-1,3,5-triazine in a yield of 33.4% and 2,4-bis(ethylamino)-6-methyl-1,3,5-triazine in a yield of 12.2%.

EXAMPLE 34

Reaction of Acetoguanamine with 1-butanol

In a stainless steel autoclave having an inner volume of 70 mL were charged 1.25 g (0.01 mol) of acetoguanamine (2,4-diamino-6-methyl-1,3,5-triazine), 25 mg of 5% Pd-C catalyst (water content 50%), and 30 mL of butanol, and after purging the inside of the reaction system sufficiently with nitrogen, 10 kg/cm$^2$ of hydrogen gas was introduced. The temperature was elevated with stirring, the reaction was carried out at a reaction temperature of 240° C. for 3 hours, followed by cooling, and the contents were quantitatively analyzed. As a result, the conversion of acetoguanamine, raw material, was 30.5%, and the products were 2-amino-4-butylamino-6-methyl-1,3,5-triazine in a yield of 17.9% and 2,4-bis(butylamino)-6-methyl-1,3,5-triazine in a yield of 11.4%.

EXAMPLE 35

Reaction of Melamine with 1-butanol

In a stainless steel autoclave having an inner volume of 200 mL were charged 4.05 g (0.032 mol) of melamine, 80 mg of ferric oxide on silica catalyst (Fe$_2$O$_3$ content 50% by weight), and 100 mL of butanol, and after purging the inside of the reaction system sufficiently with nitrogen, gas exchange was performed 5 times with 40 kg/cm$^2$ of hydrogen gas. The temperature was elevated while stirring, the reaction was carried out at a reaction temperature of 280° C. for 6 hours, followed by cooling, and the contents were quantitatively analyzed. As a result, the conversion of melamine, raw material, was 10.5%, and the products were 2,4-diamino-6-butylamino-1,3,5-triazine in a yield of 8.0%.

EXAMPLE 36

Reaction of Melamine with 1-butanol

In a stainless steel autoclave having an inner volume of 200 mL were charged 4.05 g (0.032 mol) of melamine, 80 mg of manganese oxide on silica catalyst (MnO$_2$ content 50% by weight), and 100 mL of butanol, and after purging the inside of the reaction system sufficiently with nitrogen, 1 kg/cm$^2$ of hydrogen gas was introduced. The temperature was elevated while stirring, the reaction was carried out at a reaction temperature of 280° C. for 6 hours, followed by cooling, and the contents were quantitatively analyzed. As a result, the conversion of melamine, raw material, was 9.2%, and the products were 2,4-diamino-6-butylamino-1,3,5-triazine in a yield of 7.3%.

EXAMPLE 37

Reaction of Melamine with 1-butanol

In a stainless steel autoclave having an inner volume of 200 mL were charged 4.05 g (0.032 mol) of melamine, 80 mg of molybdenum oxide on silica catalyst (MoO$_3$ content 50% by weight), and 100 mL of butanol, and after purging the inside of the reaction system sufficiently with nitrogen, 40 kg/cm$^2$ of hydrogen gas was introduced. The temperature was elevated while stirring, the reaction was carried out at a reaction temperature of 280° C. for 6 hours, followed by cooling, and the contents were quantitatively analyzed. As a result, the conversion of melamine, raw material, was 7.5%, and the products were 2,4-diamino-6-butylamino-1,3,5-triazine in a yield of 7.0%.

EXAMPLE 38

Reaction of Melamine with 1-butanol

In a stainless steel autoclave having an inner volume of 200 mL were charged 4.05 g (0.032 mol) of melamine, 80 mg of chromium oxide catalyst (CrO$_3$), and 100 mL of butanol, and after purging the inside of the reaction system sufficiently with nitrogen, 40 kg/cm$^2$ of hydrogen gas was introduced. The temperature was elevated while stirring, the reaction was carried out at a reaction temperature of 280° C. for 6 hours, followed by cooling, and the contents were quantitatively analyzed. As a result, the conversion of melamine, raw material, was 4.3%, and the products were 2,4-diamino-6-butylamino-1,3,5-triazine in a yield of 4.1%.

EXAMPLE 39

Reaction of Melamine with 1-butanol

In a stainless steel autoclave having an inner volume of 200 mL were charged 4.05 g (0.032 mol) of melamine, 80 mg of tantalum oxide catalyst (Ta$_2$O$_5$), and 100 mL of butanol, and after purging the inside of the reaction system sufficiently with nitrogen, 1 kg/cm$^2$ of hydrogen gas was introduced. The temperature was elevated while stirring, the reaction was carried out at a reaction temperature of 280° C. for 6 hours, followed by cooling, and the contents were quantitatively analyzed. As a result, the conversion of melamine, raw material, was 2.3%, and the products were 2,4-diamino-6-butylamino-1,3,5-triazine in a yield of 1.6%.

EXAMPLE 40

Reaction of Melamine with 1-butanol

In a stainless steel autoclave having an inner volume of 200 mL were charged 4.05 g (0.032 mol) of melamine, 80 mg of niobium oxide catalyst ($Nb_2O_5$), and 100 mL of butanol, and after purging the inside of the reaction system sufficiently with nitrogen, 40 kg/cm² of hydrogen gas was introduced. The temperature was elevated while stirring, the reaction was carried out at a reaction temperature of 280° C. for 6 hours, followed by cooling, and the contents were quantitatively analyzed. As a result, the conversion of melamine, raw material, was 9.6%, and the products were 2,4-diamino-6-butylamino-1,3,5-triazine in a yield of 9.6%.

COMPARATIVE EXAMPLE 1

Reaction of Melamine with 1-butanol (Comparison with Example 5)

In a stainless steel autoclave having an inner volume of 70 mL were charged 1.26 g (0.01 mol) of melamine (2,4,6-triamino-1,3,5-triazine), 25 mg of 5% Pd-C catalyst (water content 50%), and 30 mL of butanol, and after purging the inside of the reaction system sufficiently with nitrogen, the pressure in the reactor was returned to atmospheric pressure. The temperature was elevated while stirring and the reaction was carried out at a reaction temperature of 240° C. for 3 hours. After cooling, the contents were quantitatively analyzed. As a result, the conversion of melamine, raw material, was 41.2%, and the products were 2,4-diamino-6-butylamino-1,3,5-triazine in a yield of 22.6%, and 2-amino-4,6-bis(butylamino)-1,3,5-triazine in a yield of 4.1%. The recovery of the product to the conversion of the raw material (material balance) was 64.8, which was decreased considerably as compared with the recovery in the presence of hydrogen (98.8% in Example 5).

COMPARATIVE EXAMPLE 2

Reaction of Melamine with 1-butanol (Comparison with Example 3)

In a stainless steel autoclave having an inner volume of 70 mL were charged 1.26 g (0.01 mol) of melamine (2,4,6-triamino-1,3,5-triazine) and 30 mL of butanol without any catalyst, and after purging the inside of the reaction system sufficiently with nitrogen, 40 kg/cm² of hydrogen gas was introduced. The temperature was elevated while stirring and the reaction was carried out at a reaction temperature of 240° C. for 2 hours. After cooling, the contents were quantitatively analyzed. As a result, the conversion of melamine, raw material, was 99.2%, and no modified product was obtained by the reaction.

EXAMPLE 41

Reaction of Melamine with Diethylene Glycol

In a stainless steel autoclave having an inner volume of 100 mL were charged 1.26 g (10 mmol) of melamine, 25.2 mg of 5% Pd-C catalyst (water content 50%), and 30 mL of diethylene glycol, and after purging the inside of the reaction system sufficiently with nitrogen, 10 kg/cm² at normal temperature of hydrogen gas was injected. The temperature was elevated while stirring, and after reaching 260° C., the reaction was carried out for additional 2 hours at the same temperature. After cooling, the reaction mixture was taken out and quantitative analysis of the reaction products was performed under the above-described conditions for analysis. As a result, it was confirmed that the conversion of melamine, raw material, was 36.6%, and the products were 2,4-diamino-6-(5-hydroxy-3-oxapentylamino)-1,3,5-triazine in a yield of 23.5%, 2-amino-4,6-bis(5-hydroxy-3-oxapentylamino)-1,3,5-triazine in a yield of 2.0%, and 2,4,6-tris(5-hydroxy-3-oxapentylamino)-1,3,5-triazine in a yield of 1.0%.

EXAMPLE 42

Reaction of Melamine with Diethylene Glycol

The reaction was carried out in the same manner as in Example 41 except that the amount catalyst was 4 times that used in Example 41 and the reaction time was changed to 1 hour. Quantitative analysis of the reaction products performed in the same manner as in Example 41 confirmed that the conversion of melamine, raw material, was 20.5%, and the products were 2,4-diamino-6-(5-hydroxy-3-oxapentylamino)-1,3,5-triazine in a yield of 16.5% and 2-amino-4,6-bis(5-hydroxy-3-oxapentylamino)-1,3,5-triazine in a yield of 1.0%.

EXAMPLE 43

Reaction of Melamine with Diethylene Glycol

The reaction was carried out in the same manner as in Example 41 except that the hydrogen pressure in the initial stage of the reaction was set to 40 kg/cm². Quantitative analysis of the reaction products performed in the same manner as in Example 41 confirmed that the conversion of melamine, raw material, was 24.0%, and the products were 2,4-diamino-6-(5-hydroxy-3-oxapentylamino)-1,3,5-triazine in a yield of 18.5% and 2-amino-4,6-bis(5-hydroxy-3-oxapentylamino)-1,3,5-triazine in a yield of 1.0%, and 2,4,6-tris(5-hydroxy-3-oxapentylamino)-1,3,5-triazine in a yield of 0.6%.

EXAMPLE 44

Reaction of Melamine with Diethylene Glycol

The reaction was carried out in the same manner as in Example 41 except that the catalyst used was Ni/NiO on silica catalyst. Quantitative analysis of the reaction products performed in the same manner as in Example 41 confirmed that the conversion of melamine, raw material, was 23.3%, and the products were 2,4-diamino-6-(5-hydroxy-3-oxapentylamino)-1,3,5-triazine in a yield of 13.2% and 2-amino-4,6-bis(5-hydroxy-3-oxapentylamino)-1,3,5-triazine in a yield of 1.0%, and 2,4,6-tris(5-hydroxy-3-oxapentylamino)-1,3,5-triazine in a yield of 0.6%.

EXAMPLE 45

Reaction of Melamine with Diethylene Glycol

The reaction was carried out in the same manner as in Example 41 except that the catalyst used was 5% Ru-C. Quantitative analysis of the reaction products performed in the same manner as in Example 41 confirmed that the conversion of melamine, raw material, was 18.1%, and the products were 2,4-diamino-6-(5-hydroxy-3-oxapentylamino)-1,3,5-triazine in a yield of 11.4% and 2-amino-4,6-bis(5-hydroxy-3-oxapentylamino)-1,3,5-triazine in a yield of 1.0%, and 2,4,6-tris(5-hydroxy-3-oxapentylamino)-1,3,5-triazine in a yield of 0.2%.

EXAMPLE 46

Reaction of Melamine with Triethylene Glycol

In a stainless steel autoclave having an inner volume of 100 mL were charged 1.26 g (10 mmol) of melamine, 25.2 mg of 5% Pd-C catalyst (water content 50%), and 30 mL of triethylene glycol, and after purging the inside of the reaction system sufficiently with nitrogen, 10 kg/cm$^2$ at normal temperature of hydrogen gas was injected. The temperature was elevated while stirring, and after reaching 260° C., the reaction was carried out for additional 2 hours at the same temperature. After cooling, the reaction mixture was taken out and quantitative analysis of the reaction products was performed under the above-described conditions for analysis. As a result, it was confirmed that the conversion of melamine, raw material, was 13.2%, and the products were 2,4-diamino-6-(9-hydroxy-3,6-dioxaoctylamino)-1,3,5-triazine in a yield of 8.5%.

EXAMPLE 47

Reaction of Melamine with Tetraethylene Glycol

In a stainless steel autoclave having an inner volume of 100 mL were charged 1.26 g (10 mmol) of melamine, 25.2 mg of 5% Pd-C catalyst (water content 50%), and 30 mL of tetraethylene glycol, and after purging the inside of the reaction system sufficiently with nitrogen, 10 kg/cm$^2$ at room temperature of hydrogen gas was injected. The temperature was elevated while stirring, and after reaching 260° C., the reaction was carried out for additional 2 hours at the same temperature. After cooling, the reaction mixture was taken out and quantitative analysis of the reaction products was performed under the above-described conditions for analysis. As a result, it was confirmed that the conversion of melamine, raw material, was 14.6%, and the products were 2,4-diamino-6-(11-hydroxy-3,6,9-trioxaundecylamino)-1,3,5-triazine in a yield of 10.5%.

EXAMPLE 48

Reaction of Melamine with 2,3-butanediol

In a stainless steel autoclave having an inner volume of 100 mL were charged 1.26 g (10 mmol) of melamine, 25.2 mg of 5% Pd-C catalyst (water content 50%), and 30 mL of 2,3-butanediol, and after purging the inside of the reaction system sufficiently with nitrogen, 10 kg/cm$^2$ at room temperature of hydrogen gas was injected. The temperature was elevated while stirring, and after reaching 260° C., the reaction was carried out for additional 2 hours at the same temperature. After cooling, the reaction mixture was taken out and quantitative analysis of the reaction products was performed under the above-described conditions for analysis. As a result, it was confirmed that the conversion of melamine, raw material, was 27.4%, and the products were 2,4-diamino-6-(2-hydroxy-1,2-dimethylethylamino)-1,3,5-triazine in a yield of 14.6%, 2-diamino-4,6-bis(2-hydroxy-1,2-dimethylethylamino)-1,3,5-triazine in a yield of 2.3%, and 2,4,6-tris(2-hydroxy-1,2-dimethylethylamino)-1,3,5-triazine in a yield of 1.4%.

INDSUTRIAL APPLICABILITY

According to the first aspect of the present invention, substituted 1,3,5-triazine derivatives which are useful compounds and can be used as intermediates for various fine chemicals such as agricultural chemicals, medicines, dyes, coatings, and the like, or as various paints, adhesives, resin materials, flame retarding materials as well can be produced with ease and in good yield from aminotriazines of the formula (I) and alcohols of the formula (II) under relatively mild reaction conditions and by simple reaction operations and in addition by-producing only water. Similarly, according to the second aspect of the present invention, substituted 1,3,5-triazine derivatives which are useful compounds and can be used as intermediates for various fine chemicals such as agricultural chemicals, medicines, dyes, paints, and the like, or as various paints, adhesives, resin materials, flame retarding materials as well can be produced with ease and in good yields from aminotriazines of the formula (I) and dihydric alcohols of the formula (IV) under relatively mild reaction conditions and by simple reaction operations and in addition by-producing only water.

Various modified, substituted 1,3,5-triazine derivatives which are the products obtained by the present invention can be obtained as a mixture. The products can be separated in the form of high purity or pure preparations by separation methods used for general organic compounds and provided for the various applications described above.

In some application fields (in particular, as flame retardants for resins, modifying additives as a plasticizer, and the like), the reaction mixture does not have to be separated and can be used as it is Further, most of the substituted triazines which can be obtained by the reaction of the present invention, are compounds the synthesis of which has heretofore been difficult or at high costs and show interesting behaviors in light of physical properties, such as solubility in water and organic solvents, stability at high temperatures, melting points, boiling points, basicity, and the like, and their utility is expected to extend further.

What is claimed is:

1. A synthetic method of 1,3,5-triazine derivatives characterized in that a 1,3,5-triazine derivative having at least one amino group or mono-substituted amino group on a carbon atom or atoms on its ring is heated and reacted with a dihydric alcohol in the presence of a metal catalyst and hydrogen, and an alkyl group having a hydroxyl group is introduced into the at least one amino or mono-substituted amino group, wherein the 1,3,5-triazine derivative having at least one amino group or mono-substituted amino group on a carbon atom or atoms on its ring is a 1,3,5-triazine derivative of the formula (I)

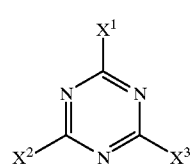

(I)

wherein at least one of $X^1$, $X^2$ and $X^3$ independently represents an $NHR^1$ group (wherein $R^1$ represents a hydrogen atom, a $C_{1-20}$ alkyl group or a phenyl group), $X^1$, $X^2$ and $X^3$ other than the at least one of $X^1$, $X^2$ and $X^3$ representing the $NHR^1$ group described above independently represent an NR²R³ group (wherein R² and R³ independently represent a $C_{1-20}$ alkyl group, or a phenyl group or R² and R³ together may form a 3- to 6-membered cyclic structure containing atoms freely selected from a carbon atom and a nitrogen atom), the dihydric alcohol is dihydric alcohol of the formula (IV)

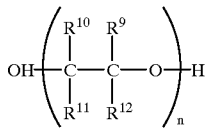

(IV)

wherein $R^9$, $R^{10}$, $R^{11}$, and $R^{12}$ independently represent a hydrogen atom or a methyl group, and n is an integer of from 1 to 5, and the metal catalyst is a solid catalyst for heterogeneous system.

2. A synthetic method of 1,3,5-triazine derivatives as claimed in claim 1, wherein the 1,3,5-triazine derivatives of the formula (I) is melamine.

3. A synthetic method of 1,3,5-triazine derivatives as claimed in claim 1, wherein the dihydric alcohol is dihydric alcohol of the formula (IV) in which $R^9$, $R^{10}$, $R^{11}$, and $R^{12}$ independently represent a hydrogen atom, and n is an integer of from 2 to 5.

4. A synthetic method of 1,3,5-triazine derivatives wherein the substituted 1,3,5-triazine derivatives obtained by the synthetic method of the claim 1 are substituted 1,3,5-triazine derivatives of the formula (III)

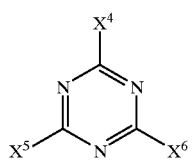

(III)

wherein at least one of $X^4$, $X^5$ and $X^6$ independently represents an $NR^5R^6$ group wherein at least one of $R^5$ and $R^6$ represents a substituent of the formula (V)

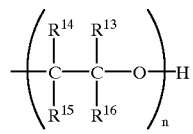

(V)

wherein $R^{13}$, $R^{14}$, $R^{15}$, and $R^{16}$ independently represent a hydrogen atom or a methyl group and n is an integer of from 1 to 5), or when either one of $R^5$ and $R^6$ is not represented by the formula (V) above, then the either one of $R^5$ and $R^6$ not represented by the formula (V) above represents a hydrogen atom, a $C_{1-20}$ alkyl group or a phenyl group, $X^4$, $X^5$, and $X^6$ other than the $NR^5R^6$ group independently represent an $NR^7R^8$ group (wherein $R^7$ and $R^8$ independently represent a hydrogen atom, a $C_{1-20}$ alkyl group or a phenyl group, or $R^7$ and $R^8$ together may form a 3- to 6-membered cyclic structure containing atoms freely selected from a carbon atom, and a nitrogen atom).

5. A synthetic method of 1,3,5-triazine derivatives as claimed in claim 1, wherein the metal catalyst used in the reaction is a catalyst containing one or more metals selected from the group consisting of chromium, mangenese, iron, cobalt, nickel, copper, niobium, molybdenum, ruthenium, rhodium, palladium, tantalum, and iridium.

6. A method of modifying 1,3,5-triazine derivatives as claimed in claim 5, wherein the matal catalyst used in the reaction is a catalyst containing one or more metals selected from the group consisting of chromium, mangenese, iron, nickel, copper, niobium, molybdenum, ruthenium, rhodium, palladium, tantalum, and iridium.

7. A synthetic method of 1,3,5-triazine derivatives as claimed in claim 1, wherein the metal catalyst used in the reaction is a catalyst containing one or more metals selected from the group consisting of chromium, mangenese, iron, cobalt, nickel, copper, niobium, molybdenum, ruthenium, rhodium, palladium, and tantalum.

8. A synthetic method of 1,3,5-triazine derivatives as claimed in claim 1, wherein the metal catalyst used in the reaction is a simple metal, oxides, hydroxides or salts.

9. A synthetic method of 1,3,5-triazine derivatives as claimed in claim 1, wherein the metal catalyst used in the reaction is a carried catalyst.

10. A synthetic method of 1,3,5-triazine derivatives as claimed in claim 1, wherein a carrier of the carried catalyst is silica, alumina, aluminosilicate, silica-alumina, zeolite, diatomaceous earth, clay mineral, active carbon or inorganic salts.

11. A synthetic method of 1,3,5-triazine derivatives as claimed in claim 1, wherein hydrogen which is present in the reaction system in the method is hydrogen gas or hydrogen-containing gas.

12. A synthetic method of 1,3,5-triazine derivatives as claimed in claim 1, wherein hydrogen which is present in the reaction system in the method is hydrogen which pre-treats the metal catalyst.

13. A synthetic method of 1,3,5-triazine derivatives as claimed in claim 1, wherein the reaction temperature is 100° C. to 500° C.

14. A synthetic method of 1,3,5-triazine derivatives as claimed in claim 1, wherein the reaction temperature is 150° C. to 400° C.

15. A synthetic method of 1,3,5-triazine derivatives as claimed in claim 4, wherein the substituted 1,3,5-triazine derivatives are 1,3,5-triazine derivatives of the formula (III) in which the $R^5$ and $R^6$ in the $NR^5R^6$ group represent independently a substituent of the formula (V)

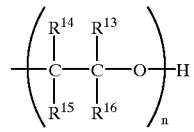

(V)

(wherein $R^{13}$, $R^{14}$, $R^{15}$, and $R^{16}$ independently represent a hydrogen atom and n is an integer of from 2 to 5), or when either one of $R^5$ and $R^6$ is not represented by the formula (V), then the either one of $R^5$ and $R^6$ not represented by the formula (V) represents a hydrogen atom, $X^4$, $X^5$, and $X^6$ other than the $NR^5R^6$ group described above independently represent an $NR^7R^8$ group (wherein $R^7$ and $R^8$ independently represent a hydrogen atom).

* * * * *